United States Patent
Ikeya et al.

(10) Patent No.: US 11,959,100 B2
(45) Date of Patent: Apr. 16, 2024

(54) METHOD FOR CULTURE OF CELLS

(71) Applicants: Kyoto University, Kyoto (JP); Takeda Pharmaceutical Company Limited, Osaka (JP)

(72) Inventors: Makoto Ikeya, Kyoto (JP); Yayoi Kamiya, Kyoto (JP)

(73) Assignees: Kyoto University, Kyoto (JP); Takeda Pharmaceutical Company Limited, Osaka (JP)

( * ) Notice: Subject to any disclaimer, the term of this patent is extended or adjusted under 35 U.S.C. 154(b) by 510 days.

(21) Appl. No.: 16/767,753

(22) PCT Filed: Nov. 29, 2018

(86) PCT No.: PCT/JP2018/043949
§ 371 (c)(1),
(2) Date: May 28, 2020

(87) PCT Pub. No.: WO2019/107485
PCT Pub. Date: Jun. 6, 2019

(65) Prior Publication Data
US 2021/0002608 A1 Jan. 7, 2021

(30) Foreign Application Priority Data
Nov. 30, 2017 (JP) ................. 2017-230074

(51) Int. Cl.
*C12N 5/0797* (2010.01)

(52) U.S. Cl.
CPC ........ *C12N 5/0623* (2013.01); *C12N 2500/30* (2013.01); *C12N 2501/11* (2013.01); *C12N 2501/115* (2013.01)

(58) Field of Classification Search
CPC .............. C12N 5/0619; C12N 2506/45; C12N 2506/08; C12N 2533/32; C12N 2501/155;
(Continued)

(56) References Cited

U.S. PATENT DOCUMENTS

| 5,580,777 A | 12/1996 | Bernard et al. |
| 6,548,059 B1 | 4/2003 | Joyce et al. |

(Continued)

FOREIGN PATENT DOCUMENTS

| CN | 102952777 A | 3/2013 |
| CN | 105483080 A | 4/2016 |

(Continued)

OTHER PUBLICATIONS

Fukuta, M. et al., "Derivation of mesenchymal stromal cells from pluripotent stem cells through a neural crest lineage using small molecule compounds with defined media.", PLOS One, 2014, 9(12):e112291.
(Continued)

*Primary Examiner* — Aaron J Kosar
(74) *Attorney, Agent, or Firm* — McCarter & English, LLP; David G. Conlin

(57) ABSTRACT

As a technique for proliferating neural crest cells without reducing differentiation capacity, provided is a method for producing neural crest cells, comprising the steps of: (1) obtaining neural crest cells; and (2) suspension-culturing the neural crest cells in a medium comprising a GSK3β inhibitor and a basic fibroblast growth factor (bFGF), wherein the medium comprises the GSK3β inhibitor with a concentration that exhibits an effect equivalent to that exhibited by CHIR99021 with a concentration of higher than 1 μM and lower than 5 μM.

17 Claims, 7 Drawing Sheets

(58) Field of Classification Search
CPC .......... C12N 2501/115; C12N 2500/38; C12N 2501/415; C12N 2506/02; C12N 2501/41; C12N 2501/01; C12N 2501/13; C12N 2501/727; C12N 2501/385; C12N 2501/999

See application file for complete search history.

(56) References Cited

U.S. PATENT DOCUMENTS

| | | |
|---|---|---|
| 10,472,607 B2 | 11/2019 | Su et al. |
| 2002/0151054 A1 | 10/2002 | Rathjen et al. |
| 2003/0003572 A1 | 1/2003 | Anderson et al. |
| 2003/0134413 A1 | 7/2003 | Rathjen et al. |
| 2006/0236415 A1 | 10/2006 | Silversides et al. |
| 2006/0281177 A1 | 12/2006 | Sieber-Blum et al. |
| 2007/0065829 A1 | 3/2007 | Lee et al. |
| 2007/0258957 A1 | 11/2007 | Bowermaster et al. |
| 2008/0014638 A1 | 1/2008 | Smith et al. |
| 2008/0213230 A1 | 9/2008 | Phillips et al. |
| 2010/0009442 A1 | 1/2010 | Sasai et al. |
| 2011/0135696 A1 | 6/2011 | Isacson et al. |
| 2012/0028351 A1 | 2/2012 | Li et al. |
| 2012/0028355 A1 | 2/2012 | Sato et al. |
| 2012/0219535 A1 | 8/2012 | Maxson, Jr. et al. |
| 2013/0280804 A1 | 10/2013 | Dalton et al. |
| 2014/0093960 A1 | 4/2014 | Tsuji et al. |
| 2014/0243227 A1 | 8/2014 | Clevers et al. |
| 2014/0248696 A1 | 9/2014 | Zhang et al. |
| 2014/0315301 A1 | 10/2014 | Hanna et al. |
| 2014/0315305 A1 | 10/2014 | Shimmura et al. |
| 2015/0010515 A1 | 1/2015 | Schoeler et al. |
| 2015/0030570 A1 | 1/2015 | Pan et al. |
| 2015/0050667 A1 | 2/2015 | Carson et al. |
| 2015/0218523 A1 | 8/2015 | Cheung |
| 2016/0215263 A1 | 7/2016 | Keller et al. |
| 2016/0230143 A1 | 8/2016 | Chen et al. |
| 2016/0237405 A1 | 8/2016 | Dalton et al. |
| 2016/0250261 A1 | 9/2016 | Chatzistergos et al. |
| 2016/0326497 A1 | 11/2016 | Stadtfeld et al. |
| 2016/0369233 A1 | 12/2016 | Graf et al. |
| 2017/0044495 A1 | 2/2017 | Nakagiri |
| 2017/0191038 A1 | 7/2017 | Deng et al. |
| 2017/0198254 A1 | 7/2017 | Zhang et al. |
| 2018/0010093 A1 | 1/2018 | Nishida et al. |
| 2018/0155682 A1 | 6/2018 | Kida et al. |
| 2018/0187147 A1 | 7/2018 | Saitou et al. |
| 2018/0311286 A1 | 11/2018 | Xiang et al. |

FOREIGN PATENT DOCUMENTS

| | | |
|---|---|---|
| CN | 106244522 A | 12/2016 |
| CN | 106867962 A | 6/2017 |
| EP | 2658966 A2 | 11/2013 |
| EP | 2845898 A1 | 3/2015 |
| JP | 6304818 B2 | 4/2018 |
| KR | 10-1445026 B1 | 9/2014 |
| KR | 10-2015-0059861 A | 6/2015 |
| KR | 10-2017-0092694 A | 8/2017 |
| LU | 92771 B1 | 1/2017 |
| WO | 2008/018190 A1 | 2/2008 |
| WO | 2010/108008 A2 | 9/2010 |
| WO | 2010/140698 A1 | 12/2010 |
| WO | 2011/144901 A1 | 11/2011 |
| WO | 2012/091978 A2 | 7/2012 |
| WO | 2012/164137 A1 | 12/2012 |
| WO | 2013/131012 A1 | 9/2013 |
| WO | 2013/165120 A1 | 11/2013 |
| WO | 2015/011031 A1 | 1/2015 |
| WO | 2015/180636 A1 | 12/2015 |
| WO | 2016/016894 A1 | 2/2016 |
| WO | 2016/099602 A1 | 6/2016 |
| WO | 2016/103269 A1 | 6/2016 |
| WO | 2016104574 A1 | 6/2016 |
| WO | 2016/179243 A1 | 11/2016 |
| WO | 2016194522 A1 | 12/2016 |
| WO | WO-2016194522 A1 * | 12/2016 ............... C12N 1/00 |
| WO | 2017/002888 A1 | 1/2017 |
| WO | 2017/099766 A1 | 1/2017 |
| WO | 2017/088830 A1 | 6/2017 |
| WO | 2020040166 A1 | 2/2020 |

OTHER PUBLICATIONS

Kerosuo, L. et al., "Crestospheres: Long-Term Maintenance of Multipotent, Premigratory Neural Crest Stem Cells.", Stem Cell Reports, 2015, 5(4):499-507.

Menendez, L. et al., "Wnt signaling and a Smad pathway blockade direct the differentiation of human pluripotent stem cells to multipotent neural crest cells.", Proc. Natl. Acad. Sci., 2011, 108(48):19240-5.

Horikiri, T. et al., "SOX10-Nano-Lantern Reporter Human iPS Cells; A Versatile Tool for Neural Crest Research.", PLoS One, 2017, 12(1):e0170342.

International Search Report corresponding to International Application No. PCT/JP18/043949 dated Feb. 26, 2019 (5 pages).

Search Report and Written Opinion corresponding to Singapore Patent Application No. 11202004964W, dated Sep. 28, 2021.

Thomas et al. "Human neural crest cells display molecular and phenotypic hallmarks of stem cells", Human Molecular Genetics, 2008, vol. 17, No. 21, pp. 3411-3425.

A. Narytnyk et al., "Differentiation of Human Epidermal Neural Crest Stem Cells (hEPI-NCSC) into Virtually Homogenous Populations of Dopaminergic Neurons," Stem Cell Rev. and Rep., vol. 10, No. 2, Jan. 8, 2014, pp. 316-326.

Supplementary European Search Report issued in European Patent Application No. 18883499.8, dated Jul. 13, 2021.

Avery et al., Methods for Derivation of Multipotent Neural Crest Cells Derived from Human Pluripotent Stem Cells. Methods Mol Biol. 2016;1341:197-208.

Fauquet et al., Differentiation of autonomic neuron precursors in vitro: cholinergic and adrenergic traits in cultured neural crest cells. J Neurosci. May 1981; 1(5):478-92.

Kawaguchi et al., Isolation and propagation of enteric neural crest progenitor cells from mouse embryonic stem cells and embryos. Development. Mar. 2010;137(5):693-704.

Kim et al., Neural crest specification by inhibition of the ROCK/Myosin II pathway. Stem Cells. Mar. 2015;33(3):674-85.

Krejci et al., Isolation and characterization of neural crest stem cells from adult human hair follicles. Folia Biol (Praha). 2010;56(4):149-57.

Nagy et al., Endothelin-3 regulates neural crest cell proliferation and differentiation in the hindgut enteric nervous system. Dev Biol. May 1, 2006;293(1):203-17.

Noisa et al., Notch signaling regulates the differentiation of neural crest from human pluripotent stem cells. J Cell Sci. May 1, 2014;127(Pt 9):2083-94.

Smith et al., Glucocorticoids stimulate adrenergic differentiation in cultures of migrating and premigratory neural crest. J Neurosci. Aug. 1984;4(8):2160-72.

Urano-Morisawa et al., Induction of osteoblastic differentiation of neural crest-derived stem cells from hair follicles. PLoS One. Apr. 6, 2017;12(4):e0174940, 19 pages.

Vasyliev et al., Large-scale expansion and characterization of human adult neural crest-derived multipotent stem cells from hair follicle for regenerative medicine applications. Exp Oncol. Sep. 2017;39(3):171-180.

Yang et al., Isolation and culture of neural crest stem cells from human hair follicles. J Vis Exp. Apr. 6, 2013;(74):3194, 4 pages.

Yu et al., Stem cells with neural crest characteristics derived from the bulge region of cultured human hair follicles. J Invest Dermatol. May 2010; 130(5):1227-36.

Columbia Office Action for Application NC2020/0007772, dated Aug. 28, 2022, 10 pages.

Achilleos et al., Neural crest stem cells: discovery, properties and potential for therapy. Cell Res. Feb. 2012;22(2):288-304.

(56) References Cited

OTHER PUBLICATIONS

Ahn et al., GSK3beta, but not GSK3alpha, inhibits the neuronal differentiation of neural progenitor cells as a downstream target of mammalian target of rapamycin complex1. Stem Cells Dev. May 15, 2014;23(10):1121-33.

Clewes et al., Human epidermal neural crest stem cells (hEPI-NCSC)-characterization and directed differentiation into osteocytes and melanocytes. Stem Cell Rev Rep. Nov. 2011;7(4):799-814.

Esfandiari et al., Glycogen synthase kinase-3 inhibition promotes proliferation and neuronal differentiation of human-induced pluripotent stem cell-derived neural progenitors. Stem Cells Dev. Nov. 20, 2012;21(17):3233-43.

Kreitzer et al., A robust method to derive functional neural crest cells from human pluripotent stem cells. Am J Stem Cells. Jun. 30, 2013;2(2):119-31.

Lu et al., Generation of integration-free and region-specific neural progenitors from primate fibroblasts. Cell Rep. May 30, 2013;3(5):1580-91.

Pfaltzgraff et al., Isolation and culture of neural crest cells from embryonic murine neural tube. J Vis Exp. Jun. 2, 2012;(64):e4134, 5 pages.

Qu et al., High-efficiency motor neuron differentiation from human pluripotent stem cells and the function of Islet-1. Nat Commun. Mar. 13, 2014;5:3449, 13 pages.

Sakaue et al., Human epidermal neural crest stem cells as a source of Schwann cells. Development. Sep. 15, 2015;142(18):3188-97.

Suemori et al., Efficient establishment of human embryonic stem cell lines and long-term maintenance with stable karyotype by enzymatic bulk passage. Biochem Biophys Res Commun. Jul. 7, 2006;345(3):926-32.

Columbian Office Action for Application No. NC2020/0007772, dated Apr. 13, 2023, 31 pages.

Chimge et al., Generation of neural crest progenitors from human embryonic stem cells. J Exp Zool B Mol Dev Evol. Mar. 1, 20105;314(2):95-103.

Lee et al., Derivation of neural crest cells from human pluripotent stem cells. Nat Protoc. Apr. 2010;5(4):688-701.

Columbian Office Action for Application No. NC2020/0007772, dated Sep. 24, 2023, 40 pages.

\* cited by examiner (A)

(B)

METHOD FOR CULTURE OF CELLS

RELATED APPLICATIONS

This application is a national stage application filed under 35 U.S.C. § 371, of International Patent Application No. PCT/JP2018/043949, filed Nov. 29, 2018, which claims the benefit of and priority to JP2017-230074, filed Nov. 30, 2017, the entire contents of which are hereby expressly incorporated by reference herein.

TECHNICAL FIELD

The present invention relates to a method for producing neural crest cells, a method for allowing neural crest cells to proliferate, a medium, a frozen stock, and a method for producing various types of cells from neural crest cells. More specifically, the present invention relates to a method for producing neural crest cells, a method for allowing neural crest cells to proliferate, a medium for use in these methods, a frozen stock comprising neural crest cells, and a method for producing various types of cells into which the differentiation of neural crest cells may be induced.

BACKGROUND ART

Neural crest cells (NCCs) are cells that develop from between the neuroectoderm and the epidermal ectoderm when the neural tube is formed from the neural plate during early development. These cells have multipotency to differentiate into many types of cells such as nerve cells, glial cells, mesenchymal stromal cells, bone cells, chondrocytes, corneal cells and pigment cells, and the ability to self-proliferate. Such multipotency and ability to self-proliferate indicate the usefulness of the neural crest cells as a cell medicament for regenerative medicine. Thus, there is a demand for a technique for efficient maintenance or proliferation of neural crest cells.

Non Patent Literature 1 states that neural crest cells are induced from human induced pluripotent stem cells (iPSCs), and mesenchymal stromal cells or the like are further induced from the neural crest cells. In Non Patent Literature 1, the neural crest cells are maintenance-cultured by adherent culture using a medium supplemented with a TGFβ inhibitor, an epidermal growth factor (EGF) and a basic fibroblast growth factor (bFGF (also referred to as FGF2)).

Non Patent Literature 2 states that neural crest cells are induced from chicken embryonic neural tube, and glial cells or the like are further induced from the neural crest cells. In Non Patent Literature 2, the neural crest cells are maintenance-cultured by suspension culture using a medium supplemented with chicken embryonic extracts, an insulin-like growth factor (IGF), bFGF and retinoic acid (RA).

Non Patent Literature 3 states that neural crest cells are induced from human embryonic stem cells (ESCs) or human iPSCs, and smooth muscular cells or the like are further induced from the neural crest cells. In Non Patent Literature 3, the neural crest cells are maintenance-cultured by adherent culture using a medium supplemented with a GSK3β inhibitor and a TGFβ inhibitor.

Non Patent Literature 4 states that neural crest cells are induced from human iPSCs and maintained by adherent culture or suspension culture using a medium supplemented with a GSK3β inhibitor, a TGFβ inhibitor, EGF and bFGF. Non Patent Literature 4 reports that the number and ratio of neural crest cells in a cultured cell population under the maintenance culture by adherent culture were decreased in a concentration-dependent manner within the bFGF concentration range of 0 pg/ml to 10 ng/ml (see FIGS. 5A to 5C). In the maintenance culture by suspension culture, the presence of Sox10-positive cells was confirmed by culture for 7 days using 1 µM CHIR99021 as the GSK3µ inhibitor. However, whether the cells had multipotency was not determined.

None of Non Patent Literatures 1 to 4 disclose that neural crest cells are maintained and allowed to proliferate by suspension culture using a medium supplemented with CHIR99021 with a concentration of higher than 1 µM and bFGF.

CITATION LIST

Non Patent Literature

Non Patent Literature 1: Fukuta M. et al., "Derivation of mesenchymal stromal cells from pluripotent stem cells through a neural crest lineage using small molecule compounds with defined media.", PLoS One, 2014, 9(12): e112291.

Non Patent Literature 2: Kerosuo L. et al., "Crestospheres: Long-Term Maintenance of Multipotent, Premigratory Neural Crest Stem Cells.", Stem Cell Reports, 2015, 5(4):499-507.

Non Patent Literature 3: Menendez L. et al., "Wnt signaling and a Smad pathway blockade direct the differentiation of human pluripotent stem cells to multipotent neural crest cells.", Proc. Natl. Acad. Sci., 2011, 108(48):19240-5.

Non Patent Literature 4: Horikiri T. et al., "SOX10-Nano-Lantern Reporter Human iPS Cells; A Versatile Tool for Neural Crest Research.", PLoS One, 2017, 12(1): e0170342.

SUMMARY OF INVENTION

Technical Problem

Neural crest cells originally possess multipotency to differentiate into many types of cells such as nerve cells, glial cells, mesenchymal stromal cells, bone cells, chondrocytes, corneal cells and pigment cells. However, the culture of the neural crest cells is known to gradually reduce the multipotency and to decrease the types of cells into which the neural crest cells can differentiate.

A main object of the present invention is to provide a technique for culture and proliferation over a long period of neural crest cells that maintain multipotency.

Solution to Problem

To attain the object, the present invention provides the following [1] to [21b].

[1] A method for producing neural crest cells, comprising the steps of:
   (1) obtaining neural crest cells; and
   (2) suspension-culturing the neural crest cells in a medium comprising a GSK3β inhibitor and a basic fibroblast growth factor (bFGF), wherein the medium comprises the GSK3β inhibitor with a concentration that exhibits an effect equivalent to that exhibited by CHIR99021 with a concentration of higher than 1 µM.

[1a] The production method according to [1], wherein the concentration of the GSK3β inhibitor is a concentration that exhibits an effect equivalent to that exhibited by CHIR99021 with a concentration of higher than 1 μM and lower than 5 μM.

[1b] The production method according to [1], wherein the effect is evaluated on the basis of GSK3β inhibitory activity of the GSK3β inhibitor, wherein the GSK3β inhibitory activity of the GSK3β inhibitor is determined by the procedures of:
  (i) culturing cells whose reporter gene expression is suppressed under the control of GSK3β, in the presence and absence of the GSK3β inhibitor;
  (ii) measuring an expression level of the reporter gene in the presence and absence of the GSK3β inhibitor; and
  (iii) determining the GSK3β inhibitory activity of the GSK3β inhibitor on the basis of an amount of increase in the expression level of the reporter gene in the presence of the GSK3β inhibitor with respect to the expression level of the reporter gene in the absence of the GSK3β inhibitor.

[2] The production method according to [1], wherein the medium further comprises a TGFβ inhibitor.

[3] The production method according to [1], wherein the medium is CDM medium.

[4] The production method according to [1], wherein the medium further comprises an epidermal growth factor (EGF).

[5] The production method according to [1], wherein the GSK3β inhibitor is at least one member selected from the group consisting of CHIR99021, CP21R7, CHIR98014, LY2090314, kenpaullone, AR-A0144-18, TDZD-8, SB216763, BIO, TWS-119 and SB415286.

[6] The production method according to [5], wherein the GSK3β inhibitor is CHIR99021.

[6a] The production method according to [6], wherein the CHIR99021 has a concentration of higher than 1 μM and lower than 5 μM.

[6b] The production method according to [6a], wherein the CHIR99021 has a concentration of 2 or higher and 4.5 μM or lower.

[6c] The production method according to [5], wherein the GSK3β inhibitor is CP21R7.

[6d] The production method according to [6c], wherein the CP21R7 has a concentration of 0.5 or higher and 1 μM or lower.

[7] The production method according to [2], wherein the TGFβ inhibitor is at least one member selected from the group consisting of SB431542, A83-01, LDN193189, Wnt3a/BIO, BMP4, GW788388, SM16, IN-1130, GW6604 and SB505124.

[7a] The production method according to any of [1] to [7], wherein the bFGF has a concentration of 20 to 40 ng/ml.

[8] The production method according to [1], wherein in the step (2), the neural crest cells are passaged every 5 to 8 days after inoculation.

[9] The production method according to [1], wherein the step (1) is the step of inducing the differentiation of stem cells into the neural crest cells.

[10] A method for proliferating neural crest cells, comprising the step of:
  (I) suspension-culturing the neural crest cells in a medium comprising a GSK3β inhibitor and a basic fibroblast growth factor (bFGF), wherein the medium comprises the GSK3β inhibitor with a concentration that exhibits an effect equivalent to that exhibited by CHIR99021 with a concentration of higher than 1 μM.

[10a] The proliferation method according to [10], wherein the concentration of the GSK3β inhibitor is a concentration that exhibits an effect equivalent to that exhibited by CHIR99021 with a concentration of higher than 1 μM and lower than 5 μM.

[10b] The proliferation method according to [10], wherein the medium further comprises a TGFβ inhibitor.

[10c] The proliferation method according to [10], wherein the medium is CDM medium.

[10d] The proliferation method according to [10], wherein the medium further comprises an epidermal growth factor (EGF).

[10e] The proliferation method according to [10], wherein the GSK3β inhibitor is at least one member selected from the group consisting of CHIR99021, CP21R7, CHIR98014, LY2090314, kenpaullone, AR-A0144-18, TDZD-8, SB216763, BIO, TWS-119 and SB415286.

[10f] The proliferation method according to [10e], wherein the GSK3β inhibitor is CHIR99021.

[10g] The proliferation method according to [10f], wherein the CHIR99021 has a concentration of higher than 1 μM and lower than 5 μM.

[10h] The proliferation method according to [10g], wherein the CHIR99021 has a concentration of 2 or higher and 4.5 μM or lower.

[10i] The proliferation method according to [10e], wherein the GSK3β inhibitor is CP21R7.

[10j] The proliferation method according to [10i], wherein the CP21R7 has a concentration of 0.5 or higher and 1 μM or lower.

[10k] The proliferation method according to [10b], wherein the TGFβ inhibitor is at least one member selected from the group consisting of SB431542, A83-01, LDN193189, Wnt3a/BIO, BMP4, GW788388, SM16, IN-1130, GW6604 and SB505124.

[10l] The proliferation method according to [10], wherein in the step (I), the neural crest cells are passaged every 5 to 8 days after inoculation.

[11] A medium comprising a GSK3β inhibitor, a basic fibroblast growth factor (bFGF) and neural crest cells, wherein the medium comprises the GSK3β inhibitor with a concentration that exhibits an effect equivalent to that exhibited by CHIR99021 with a concentration of higher than 1 μM.

[11a] The medium according to [11], wherein the concentration of the GSK3β inhibitor is a concentration that exhibits an effect equivalent to that exhibited by CHIR99021 with a concentration of higher than 1 μM and lower than 5 μM.

[12] The medium according to [11], further comprising a TGFβ inhibitor.

[13] The medium according to [11], wherein the medium is CDM medium.

[14] The medium according to [11], further comprising an epidermal growth factor (EGF).

[15] The medium according to [11], wherein the GSK3β inhibitor is at least one member selected from the group consisting of CHIR99021, CP21R7, CHIR98014, LY2090314, kenpaullone, AR-A0144-18, TDZD-8, SB216763, BIO, TWS-119 and SB415286.

[16] The medium according to [15], wherein the GSK3β inhibitor is CHIR99021.

[16a] The medium according to [16], wherein the CHIR99021 has a concentration of higher than 1 μM and lower than 5 μM.

[16b] The medium according to [16a], wherein the CHIR99021 has a concentration of 2 or higher and 4.5 μM or lower.

[16c] The medium according to [15], wherein the GSK3β inhibitor is CP21R7.

[16d] The medium according to [16c], wherein the CP21R7 has a concentration of 0.5 or higher and 1 μM or lower.

[17] The medium according to [12], wherein the TGF inhibitor is at least one member selected from the group consisting of SB431542, A83-01, LDN193189, Wnt3a/BIO, BMP4, GW788388, SM16, IN-1130, GW6604 and SB505124.

[18] A frozen stock comprising neural crest cells obtained by a production method according to [1].

[18a] The frozen stock according to [18], wherein the frozen stock is obtained by the steps of: separating the neural crest cells obtained by the steps of the production method according to [1]; and suspending the separated neural crest cells in a cell preservation solution, followed by freezing.

[19] A method for producing nerve cells, glial cells, mesenchymal stromal cells, bone cells, chondrocytes, corneal cells or pigment cells, comprising the steps of:
(i) suspension-culturing neural crest cells in a medium comprising a GSK3β inhibitor and a basic fibroblast growth factor (bFGF), wherein the medium comprises the GSK3β inhibitor with a concentration that exhibits an effect equivalent to that exhibited by CHIR99021 with a concentration of higher than 1 μM; and
(ii) differentiating the neural crest cells obtained in the step (i) into cells of at least one lineage selected from the group consisting of nerve cells, glial cells, mesenchymal stromal cells, bone cells, chondrocytes, corneal cells and pigment cells.

[19a] The production method according to [19], wherein the concentration of the GSK3β inhibitor is a concentration that exhibits an effect equivalent to that exhibited by CHIR99021 with a concentration of higher than 1 μM and lower than 5 μM.

[19b] The production method according to [19], wherein the medium further comprises a TGFβ inhibitor.

[19c] The production method according to [19], wherein the medium is CDM medium.

[19d] The production method according to [19], wherein the medium further comprises an epidermal growth factor (EGF).

[19e] The production method according to [19], wherein the GSK3β inhibitor is at least one member selected from the group consisting of CHIR99021, CP21R7, CHIR98014, LY2090314, kenpaullone, AR-A0144-18, TDZD-8, SB216763, BIO, TWS-119 and SB415286.

[19f] The production method according to [19e], wherein the GSK3β inhibitor is CHIR99021.

[19g] The production method according to [19f], wherein the CHIR99021 has a concentration of higher than 1 μM and lower than 5 μM.

[19h] The medium according to [19g], wherein the CHIR99021 has a concentration of 2 or higher and 4.5 μM or lower.

[19i] The medium according to [19e], wherein the GSK3β inhibitor is CP21R7.

[19j] The production method according to [19i], wherein the CP21R7 has a concentration of 0.5 or higher and 1 μM or lower.

[19k] The production method according to [19b], wherein the TGFβ inhibitor is at least one member selected from the group consisting of SB431542, A83-01, LDN193189, Wnt3a/BIO, BMP4, GW788388, SM16, IN-1130, GW6604 and SB505124.

[19l] The production method according to [19], wherein in the step (I), the neural crest cells are passaged every 5 to 8 days after inoculation.

[20] A method for culturing neural crest cells having multipotency for a long period, comprising the steps of:
(1) obtaining neural crest cell; and
(2) suspension-culturing the neural crest cells in a medium comprising a GSK3β inhibitor and a basic fibroblast growth factor, wherein the medium comprises the GSK3β inhibitor with a concentration that exhibits an effect equivalent to that exhibited by CHIR99021 with a concentration of higher than 1 μM.

[20a] The culture method according to [20], wherein the concentration of the GSK3β inhibitor is a concentration that exhibits an effect equivalent to that exhibited by CHIR99021 with a concentration of higher than 1 μM and lower than 5 μM.

[20b] The culture method according to [20], wherein the medium further comprises a TGFβ inhibitor.

[20c] The culture method according to [20], wherein the medium is CDM medium.

[20d] The culture method according to [20], wherein the medium further comprises an epidermal growth factor (EGF).

[20e] The culture method according to [20], wherein the GSK3β inhibitor is at least one member selected from the group consisting of CHIR99021, CP21R7, CHIR98014, LY2090314, kenpaullone, AR-A0144-18, TDZD-8, SB216763, BIO, TWS-119 and SB415286.

[20f] The culture method according to [20e], wherein the GSK3β inhibitor is CHIR99021.

[20g] The culture method according to [20f], wherein the CHIR99021 has a concentration of higher than 1 μM and lower than 5 μM.

[20h] The culture method according to [20g], wherein the CHIR99021 has a concentration of 2 or higher and 4.5 μM or lower.

[20i] The culture method according to [20e], wherein the GSK3β inhibitor is CP21R7.

[20j] The culture method according to [20i], wherein the CP21R7 has a concentration of 0.5 or higher and 1 μM or lower.

[20k] The culture method according to [20b], wherein the TGFβ inhibitor is at least one member selected from the group consisting of SB431542, A83-01, LDN193189, Wnt3a/BIO, BMP4, GW788388, SM16, IN-1130, GW6604 and SB505124.

[20l] The culture method according to [20], wherein in the step (I), the neural crest cells are passaged every 5 to 8 days after inoculation.

[21] Use of a medium comprising a basic fibroblast growth factor and a GSK3β inhibitor with a concentration that exhibits an effect equivalent to that exhibited by CHIR99021 with a concentration of higher than 1 μM, for culturing neural crest cells having multipotency for a long period.

[21a] Use of a basic fibroblast growth factor and a GSK3β inhibitor with a concentration that exhibits an effect equivalent to that exhibited by CHIR99021 with a concentration of higher than 1 μM, for culturing neural crest cells.

[21b] Use of a basic fibroblast growth factor and a GSK3β inhibitor with a concentration that exhibits an effect equivalent to that exhibited by CHIR99021 with a concentration of higher than 1 μM, for producing a neural crest cell medium.

As used herein, "pluripotency" means the ability to be able to differentiate into tissues and cells having various different shapes and functions and to be able to differentiate into cells of any lineage of the 3 germ layers. "Pluripotency" is different from "totipotency", which is the ability to be able to differentiate into any tissue of the living body, including the placenta, in that pluripotent cells cannot differentiate into the placenta and therefore, do not have the ability to form an individual.

"Multipotency" means the ability to be able to differentiate into plural and limited numbers of linages of cells. For example, mesenchymal stem cells, hematopoietic stem cells, neural stem cells are multipotent, but not pluripotent. Neural crest cells have multipotency to differentiate into cells such as nerve cells, glial cells, mesenchymal stromal cells, bone cells, chondrocytes, corneal cells and pigment cells.

As used herein, "culture" refers to maintenance, proliferation (growth), and/or differentiation of cells in in vitro environment. "Culturing" means maintaining cells and/or allowing the cells to proliferate (grow) and/or differentiate out of tissue or the body, for example, in a cell culture dish or a flask.

"Adherent culture" means culture in a state where cells are attached to a container, for example, in a state where cells are attached to a cell culture dish or a flask made of a sterilized plastic (or coated plastic) in the presence of an appropriate medium.

"Suspension culture" means culture in a state where cells are dispersed as single cells or as cell spheres each consisting of two or more cells in an appropriate medium without being attached to a container.

"Expansion culture" means culture with the aim of allowing desired cells to proliferate.

"GSK3β inhibitor" is a substance having inhibitory activity against GSK3β (glycogen synthase kinase 3β). GSK3 (glycogen synthase kinase 3) is a serine/threonine protein kinase and involved in many signaling pathways associated with the production of glycogen, apoptosis, maintenance of stem cells, etc. GSK3 has the 2 isoforms α and β. "GSK3β inhibitor" used in the present invention is not particularly limited as long as the GSK3β inhibitor has GSK3β inhibitory activity. The GSK3β inhibitor may be a substance having both GSK3β inhibitory activity and GSK3α inhibitory activity.

"TGFβ inhibitor" is a substance having inhibitory activity against TGFβ (transforming growth factor (3). TGFβ is a cytokine binding to two types of serine/threonine protein kinase receptors and controls cell proliferation, cell differentiation, cell death, etc. via signal transduction, mainly, for activating Smad (R-Smad). Examples of the substance having TGFβ inhibitory activity include substances inhibiting the binding of TGFβ to its receptor, and substances inhibiting downstream signals after the binding of TGFβ to its receptor. Examples of the downstream signals include the phosphorylation of TGFβI receptor by TGFβII receptor, and the phosphorylation of Smad by phosphorylated TGFβI receptor. "TGFβ inhibitor" used in the present invention is not particularly limited as long as the TGFβ inhibitor has TGFβ inhibitory activity.

As used herein, "marker" is "marker protein" or "marker gene" and means a protein that is specifically expressed on cell surface, in cytosol, and/or in nucleus of a predetermined cell type, or a gene thereof. The marker may be a positive selection marker or a negative selection marker. Preferably, the marker is a cell surface marker. Particularly, a cell surface-positive selection marker allows concentration, isolation, and/or detection of living cells.

The marker protein can be detected by use of immunological assay, for example, ELISA, immunostaining, or flow cytometry, using an antibody specific for the marker protein. An antibody that binds to a specific amino acid sequence of the marker protein or a specific sugar chain linked to the marker protein, etc. can be used as the antibody specific for the marker protein. In case of an intracellularly expressed marker protein which does not appear on the surface of cells (for example, a transcription factor or a subunit thereof), the marker protein of interest can be detected by expressing the marker protein with a reporter protein and detecting the reporter protein (for example, Non Patent Literature 4). This method may be preferably used when an appropriate cell surface marker is not found. The marker gene can be detected by use of a method of amplifying and/or detecting nucleic acid known in the art, for example, RT-PCR, microarray, biochip, or RNAseq.

As used herein, "expression" is defined as transcription and/or translation of a certain nucleotide sequence driven by an intracellular promoter.

As used herein, the term "comprise(s)" or "comprising" refers to inclusion of the element(s) following the word without limitations thereto. Thus, this suggests inclusion of the element(s) following the word, but does not suggest exclusion of any other element.

As used herein, the term "about" or "around" refers to a value which may vary up to plus or minus 30%, 25%, 20%, 15%, 10%, 8%, 6%, 5%, 4%, 3%, 2%, or 1% from the reference value. Preferably, the term "about" or "around" refers to a range from minus or plus 15%, 10%, 5%, or 1% from the reference value.

Advantageous Effects of Invention

The present invention provides a technique for culture and proliferation over a long period of neural crest cells that maintain multipotency.

DESCRIPTION OF EMBODIMENTS

Figure 1:
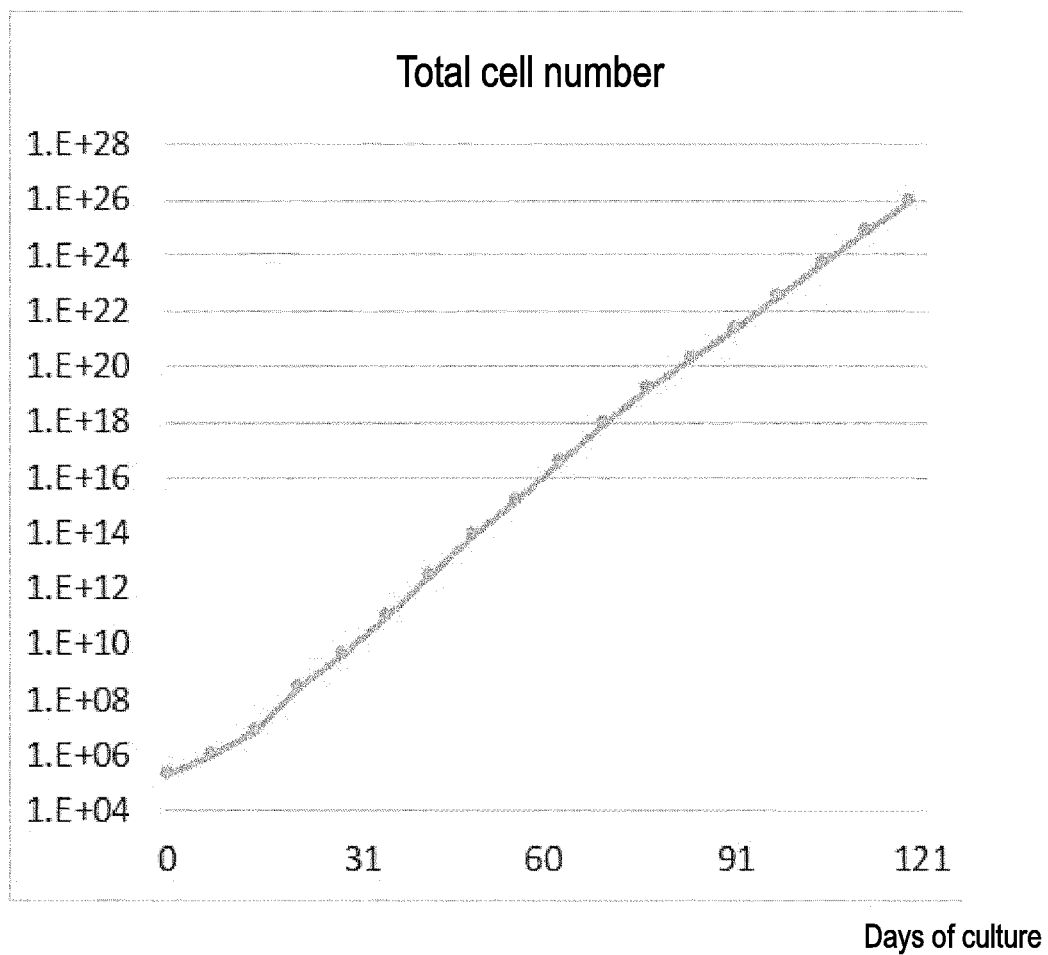
FIG. 1 is a graph showing change in total cell number after the start of expansion culture of neural crest cells (Example 1). The ordinate shows the total cell number, and "1.E+" represents a multiplier of 10. For example, "1.E+04" means 10000 cells. The abscissa shows days of culture.

Hereinafter, suitable modes for carrying out the present invention will be described. The embodiments described below are given merely for illustrating typical embodiments of the present invention. The scope of the present invention should not be interpreted as being limited by these embodiments.

[Method for Producing Neural Crest Cells and Method for Proliferating Neural Crest Cells]

The method for producing neural crest cells according to the present invention comprises the steps given below. Of these steps, the step (2) is particularly the method for proliferating neural crest cells according to the present invention.
(1) Obtaining neural crest cells; and
(2) suspension-culturing the neural crest cells in a medium comprising a GSK3β inhibitor and a basic fibroblast growth factor (bFGF), wherein the medium comprises the GSK3β inhibitor with a concentration that exhibits an effect equivalent to that exhibited by CHIR99021 with a concentration of higher than 1 μM.

[Step (1) of Obtaining Neural Crest Cells]

The step (1) of obtaining neural crest cells is the step of obtaining neural crest cells to be subjected to step (2). Examples of the method for obtaining the neural crest cells in the step (1) include, but are not particularly limited to, a method of inducing the differentiation of stem cells into the neural crest cells, a method of purchasing commercially available neural crest cells, and a method of collecting naturally occurring neural crest cells.

In one embodiment of the present invention, in order to obtain the neural crest cells to be subjected to step (2), the differentiation of stem cells into the neural crest cells can be induced.

Examples of the "stem cells" that may be used in the present invention include pluripotent stem cells. The "pluripotent stem cells" that may be used in the present invention refer to stem cells that can differentiate into tissues and cells having various different shapes and functions and have the ability to differentiate into cells of any lineage of the 3 germ layers (endoderm, mesoderm, and ectoderm). Examples thereof include, but are not particularly limited to, embryonic stem cells (ESCs), embryonic stem cells derived from cloned embryos obtained by nuclear transplantation, spermatogonial stem cells, embryonic germ cells, and induced pluripotent stem cells (herein also referred to as "iPSCs"). The "multipotent stem cells" that may be used in the present invention refer to stem cells having the ability to be able to differentiate into plural and limited numbers of linages of cells. Examples of the "multipotent stem cells" that may be used in the present invention include dental pulp stem cells, oral mucosa-derived stem cells, hair follicle stem cells, and somatic stem cells derived from cultured fibroblasts or bone marrow stem cells. The pluripotent stem cells are preferably ESCs and iPSCs.

Available "ESCs" include murine ESCs such as various murine ESC lines established by inGenious Targeting Laboratory, Riken (Institute of Physical and Chemical Research), and the like, and human ESCs such as various human ESC lines established by University of Wisconsin, NIH, Riken, Kyoto University, National Center for Child Health and Development, Cellartis, and the like. For example, CHB-1 to CHB-12 lines, RUES1 line, RUES2 line, and HUES1 to HUES28 lines distributed by ESI Bio, H1 line and H9 line distributed by WiCell Research, and KhES-1 line, KhES-2 line, KhES-3 line, KhES-4 line, KhES-5 line, SSES1 line, SSES2 line, and SSES3 line distributed by Riken can be used as the human ESC lines.

The "induced pluripotent stem cells" refer to cells that are obtained by reprograming mammalian somatic cells or undifferentiated stem cells by introducing particular factors (nuclear reprogramming factors). At present, there are various "induced pluripotent stem cells" and iPSCs established by Yamanaka, et al. by introducing the 4 factors Oct3/4, Sox2, Klf4, c-Myc into murine fibroblasts (Takahashi K, Yamanaka S., Cell, (2006) 126: 663-676); iPSCs derived from human cells, established by introducing similar 4 factors into human fibroblasts (Takahashi K, Yamanaka S., et al. Cell, (2007) 131: 861-872.); Nanog-iPSCs established by sorting cells using expression of Nanog as an indicator after introduction of the 4 factors (Okita, K., Ichisaka, T., and Yamanaka, S. (2007). Nature 448, 313-317.); iPSCs produced by a method not using c-Myc (Nakagawa M, Yamanaka S., et al. Nature Biotechnology, (2008) 26, 101-106); iPSCs established by introducing 6 factors by a virus-free method (Okita K et al. Nat. Methods 2011 May; 8(5): 409-12, Okita K et al. Stem Cells. 31 (3) 458-66); and the like may be also used. Also, induced pluripotent stem cells established by introducing the 4 factors OCT3/4, SOX2, NANOG, and LIN28 by Thomson et al. (Yu J., Thomson J A. et al., Science (2007) 318: 1917-1920.); induced pluripotent stem cells produced by Daley et al. (Park I H, Daley G Q. et al., Nature (2007) 451: 141-146); induced pluripotent stem cells produced by Sakurada et al. (Japanese Unexamined Patent Application Publication No. 2008-307007) and the like may be used.

In addition, any of known induced pluripotent stem cells known in the art described in all published articles (for example, Shi Y., Ding S., et al., Cell Stem Cell, (2008) Vol 3, Issue 5, 568-574; Kim J B., Scholer H R., et al., Nature, (2008) 454, 646-650; Huangfu D., Melton, D A., et al., Nature Biotechnology, (2008) 26, No. 7, 795-797) or patents (for example, Japanese Unexamined Patent Application Publication No. 2008-307007, Japanese Unexamined Patent Application Publication No. 2008-283972, U52008-2336610, U52009-047263, WO2007-069666, WO2008-

118220, WO2008-124133, WO2008-151058, WO2009-006930, WO2009-006997, WO2009-007852).

Available induced pluripotent cell lines include various iPSC lines established by NIH, Riken, Kyoto University and the like. Examples of such human iPSC lines include HiPS-RIKEN-1A line, HiPS-RIKEN-2A line, HiPS-RIKEN-12A line, and Nips-B2 line from Riken, and 253G1 line, 253G4 line, 1201C1 line, 1205D1 line, 1210B2 line, 1383D2 line, 1383D6 line, 201B7 line, 409B2 line, 454E2 line, 606A1 line, 610B1 line, 648A1 line, 1231A3 line, and FfI-01s04 line from Kyoto University. 1231A3 line is preferred.

The induction of the differentiation of stem cells into the neural crest cells can be performed according to a known method described in a literature (for example, Non Patent Literature 1). In the case of using, for example, human iPSCs, the iPSCs are inoculated to a dish or the like, adherent-cultured, and then adherent-cultured in a medium comprising a TGFβ inhibitor and a GSK3β inhibitor, and can thereby be allowed to differentiate into the neural crest cells.

In this respect, the medium used is not particularly limited, and, for example, TeSR1 medium and chemically defined medium (CDM) medium are suitably used. In addition, BME medium, BGJb medium, CMRL 1066 medium, Glasgow MEM medium, improved MEM (IMEM) medium, improved MDM (IMDM) medium, Medium 199 medium, Eagle MEM medium, αMEM medium, DMEM medium (high glucose or low glucose), DMEM/F12 medium, Ham's medium, RPMI 1640 medium, Fischer's medium, and a mixed medium thereof, etc. may be used.

The CDM medium is not particularly limited, and, for example, a medium prepared from Iscove's modified Dulbecco's medium (manufactured by GE Healthcare Japan Corp.) may be used. As a more specific example, CDM medium described in Non Patent Literature 1 is used. The CDM medium may contain apotransferrin, monothioglycerol, bovine serum albumin (BSA), insulin and/or an antibiotic.

The culture period before addition of the TGFβ inhibitor and the GSK3β inhibitor can be a period in which the cell number of interest is obtained. This culture period is not particularly limited and is, for example, 2 to 6 days.

Examples of the TGFβ inhibitor include SB431542 (4-(5-benzole[1,3]dioxol-5-yl-4-pyridin-2-yl-1H-imidazol-2-yl)-benzamide, 4-[4-(1,3-benzodioxol-5-yl)-5-(2-pyridinyl)-1H-imidazol-2-yl]-benzamide, 4-[4-(3,4-methylenedioxyphenyl)-5-(2-pyridyl)-1H-imidazol-2-yl]-benzamide), A83-01 (3-(6-methylpyridin-2-yl)-1-phenylthiocarbamoyl-4-quinolin-4-ylpyrazole), LDN193189 (4-[6-[4-(1-piperazinyl)phenyl]pyrazolo[1,5-a]pyrimidin-3-yl]-quinoline), Wnt3a/BIO (Wnt Family Member 3A/(2'Z,3'E)-6-bromoindirubin-3'-oxime), BMP4 (bone morphogenetic protein 4), GW788388 (4-[4-[3-(pyridin-2-yl)-1H-pyrazol-4-yl]-pyridin-2-yl]-N-(tetrahydro-2H-pyran-4-yl)benzamide), SM16 (4-[4-(1,3-benzodioxol-5-yl)-5-(6-methyl-2-pyridinyl)-1H-imidazol-2-yl]-bicyclo[2.2.2]octane-1-carboxamide), IN-1130 (3-[[5-(6-methyl-2-pyridinyl)-4-(6-quinoxalinyl)-1H-imidazol-2-yl]methyl]-benzamide), GW6604 (2-phenyl-4-[3-(pyridin-2-yl)-1H-pyrazol-4-yl]pyridine) and SB505124 (2-(5-benzo[1,3]dioxol-5-yl-2-tert-butyl-3H-imidazol-4-yl)-6-methylpyridine). Two or more of these substances may be used in combination.

The concentration of the TGFβ inhibitor to be added in this step is appropriately adjusted depending on the type of the TGFβ inhibitor to be added, and is, for example, 1 to 40 μM, preferably 5 to 20 μM.

In the case of using SB431542 (4-[4-(1,3-benzodioxol-5-yl)-5-(2-pyridinyl)-1H-imidazol-2-yl]-benzamide), the concentration of the TGFβ inhibitor to be added can be particularly set to 10 μM.

Examples of the GSK3β inhibitor include CHIR98014 (2-[[2-[(5-nitro-6-aminopyridin-2-yl)amino]ethyl]amino]-4-(2,4-dichlorophenyl)-5-(1H-imidazol-1-yl)pyrimidine), CHIR99021 (6-[[2-[[4-(2,4-dichlorophenyl)-5-(4-methyl-1H-imidazol-2-yl)-2-pyrimidinyl]amino]ethyl]amino]nicotinonitrile), CP21R7 (3-(3-amino-phenyl)-4-(1-methyl-1H-indol-3-yl)-pyrrole-2,5-dione), LY2090314 (3-[9-fluoro-1,2,3,4-tetrahydro-2-(1-piperidinylcarbonyl)pyrrolo[3,2,1-jk][1,4]benzodiazepin-7-yl]-4-imidazo[1,2-a]pyridin-3-yl-1h-pyrrole-2,5-dione), TDZD-8 (4-benzyl-2-methyl-1,2,4-thiadiazolidine-3,5-dione), SB216763 (3-(2,4-dichlorophenyl)-4-(1-methyl-1H-indol-3-yl)-1H-pyrrole-2,5-dione), TWS-119 (3-[6-(3-aminophenyl)-7H-pyrrolo[2,3-d]pyrimidin-4-yloxy]phenol), kenpaullone, 1-azakenpaullone, SB415286 (3-[(3-chloro-4-hydroxyphenyl)amino]-4-(2-nitrophenyl)-1H-pyrrole-2,5-dione), AR-A0144-18 (1-[(4-methoxyphenyl)methyl]-3-(5-nitro-1,3-thiazol-2-yl)urea), CT99021, CT20026, BIO ((2'Z,3'E)-6-bromoindirubin-3'-oxime), BIO-acetoxime, pyridocarbazole-ruthenium cyclopentadienyl complex, OTDZT, alpha-4-dibromoacetophenone, and lithium. Two or more of these substances may be used in combination.

The GSK3β inhibitor is not limited to these substances, and antisense oligonucleotides and siRNA against GSK3β mRNA, antibodies binding to GSK3β, dominant negative GSK3β mutants, and the like can also be used as the GSK3β inhibitor. These GSK3β inhibitors are commercially available or can be synthesized according to a known method.

The concentration of the GSK3β inhibitor to be added in this step is appropriately adjusted depending on the type of the GSK3β inhibitor to be added, and is, for example, 0.01 to 20 μM, preferably 0.1 to 10 μM.

In the case of using CHIR99021, the concentration of the GSK3β inhibitor to be added is not particularly limited and can be, for example, 0.1 to 1 μM, preferably 0.5 to 1 μM, particularly, 1 μM.

The culture period after addition of the TGFβ inhibitor and the GSK3β inhibitor can be a period in which the cell number of interest is obtained. This culture period is not particularly limited and is, for example, 6 to 14 days, 8 to 12 days, 9 to 11 days or 10 days.

For the adherent culture, a culture container, for example, a dish, a flask, a microplate, or a cell culture sheet such as OptiCell (product name) (Nunc), is used. The culture container is preferably surface-treated in order to improve adhesiveness to cells (hydrophilicity), or coated with a substrate for cell adhesion such as collagen, gelatin, poly-L-lysine, poly-D-lysine, laminin, fibronectin, Matrigel (for example, BD Matrigel (Nippon Becton Dickinson Company, Ltd.)), or vitronectin.

The "Matrigel" is a soluble basement membrane preparation extracted from Engelbreth-Holm-Swarm (EHS) mouse sarcoma rich in extracellular matrix protein. The Matrigel-coated culture container is commercially available. The Matrigel is composed mainly of laminin, collagen IV, proteoglycan heparan sulfate, and entactin/nidogen-1,2. The Matrigel contains, in addition to these main components, TGFβ, an epithelial cell growth factor, an insulin-like growth factor, a fibroblast growth factor, tissue plasminogen activators 3,4, and other growth factors naturally produced in EHS tumor.

The culture temperature is not particularly limited and is 30 to 40° C. (for example, 37° C.). A carbon dioxide concentration in the culture container is on the order of, for example, 5%.

In one embodiment of the present invention, in order to obtain the neural crest cells to be subjected to step (2), commercially available neural crest cells may be purchased. Examples of the commercially available neural crest cells include Human Hair Follicle Outer Root Sheath Cells (manufactured by Cosmo Bio Co., Ltd.) and O9-1 Mouse Cranial Neural Crest Cell Line (manufactured by Merck Millipore).

In one embodiment of the present invention, in order to obtain the neural crest cells to be subjected to step (2), naturally occurring neural crest cells may be collected. Neural crest cells reportedly exist in mammalian living bodies, for example, human embryonic neural tube around 30 days after fertilization, mouse embryonic neural tube around the 9th fetal day, and human, swine and rodent adult skin (Betters et al., Developmental biology, 2010, 344 (2): 578-592; Jiang et al., Development, 2000, 127 (8): 1607-1616; Dupin et al., Developmental biology, 2012, 366 (1): 83-95; and Nagoshi et al., Cell Stem Cell 2, April 2008, 392-403). Such neural crest cells may be collected by use of a known method (for example, Motohashi et al., Biology open, 2016, 5: 311-322; and Pfaltzgraff et al., Journal of Visualized Experiments, 2012, 64: 4134) and subjected to step (2).

[Step (2) of Expansion-Culturing Neural Crest Cells]

The step (2) of expansion-culturing the neural crest cells is the step of suspension-culturing the neural crest cells in a medium comprising a GSK3β inhibitor and a basic fibroblast growth factor (bFGF).

In this respect, the medium used is not particularly limited, and, for example, CDM medium is suitably used. In addition, TeSR1 medium, BME medium, BGJb medium, CMRL 1066 medium, Glasgow MEM medium, improved MEM (IMEM) medium, improved MDM (IMDM) medium, Medium 199 medium, Eagle MEM medium, αMEM medium, DMEM medium (high glucose or low glucose), DMEM/F12 medium, Ham's medium, RPMI 1640 medium, Fischer's medium, and a mixed medium thereof, etc. may be used.

The GSK3β inhibitor mentioned above can be used without particularly limitations.

The GSK3β inhibitor is preferably at least one member selected from the group consisting of CHIR99021, CP21R7, CHIR98014, LY2090314, kenpaullone, AR-A0144-18, TDZD-8, SB216763, BIO, TWS-119 and SB415286. The GSK3β inhibitor is particularly preferably CHIR99021 or CP21R7.

The concentration of the GSK3β inhibitor to be added in this step is a concentration that exhibits an effect equivalent to that exhibited by CHIR99021 with a concentration of higher than 1 WI (or a concentration of higher than 1 µM and lower than 5 µM). CHIR99021 itself may be used as the GSK3β inhibitor. In the case of using CHIR99021 itself as the GSK3β inhibitor, as mentioned later, the suitable concentration of the GSK3β inhibitor to be added is a concentration of higher than 1 µM, preferably 2 µM or higher and lower than 5 µM, more preferably higher than 2 µM and 4.5 µM or lower, particularly preferably 3 µM or higher and 4.5 µM or lower. Thus, in the case of using a GSK3β inhibitor other than CHIR99021 in this step, the concentration of the GSK3β inhibitor to be added is a concentration that exhibits an effect equivalent to that exhibited by CHIR99021 with a concentration of higher than 1 µM, preferably a concentration that exhibits an effect equivalent to that exhibited by 2 µM or higher and lower than 5 µM CHIR99021, more preferably with a concentration that exhibits an effect equivalent to that exhibited by higher than 2 µM and 4.5 µM or lower CHIR99021, particularly preferably a concentration that exhibits an effect equivalent to that exhibited by 3 µM or higher and 4.5 µM or lower CHIR99021.

Neural crest cells that maintain multipotency can be cultured and allowed to proliferate over a culture period as long as more than 9 weeks (63 days) by suspension-culturing the neural crest cells in the presence of the GSK3β inhibitor having the concentration and bFGF.

In one embodiment of the present invention, the "neural crest cells that maintain multipotency" have differentiation capacity into nerve cells, glial cells and mesenchymal stromal cells or differentiation capacity into these cells as well as bone cells, chondrocytes, corneal cells and pigment cells.

The "neural crest cells that maintain multipotency" can be evaluated by a plurality of methods. Examples of the methods include, but are not particularly limited to, a method of inducing the differentiation of the neural crest cells to be evaluated into each lineage such as nerve cells, glial cells and mesenchymal stromal cells. Provided that the neural crest cells to be evaluated can actually be differentiated into nerve cells, glial cells and mesenchymal stromal cells, etc., the neural crest cells to be evaluated can be determined as the "neural crest cells that maintain multipotency". Another example of the method includes a method of measuring the expression of a marker protein or gene. Provided that a transcription factor SOX10 is expressed in the neural crest cells to be evaluated, the neural crest cells to be evaluated can be determined as the "neural crest cells that maintain multipotency". SOX10 can be detected by use of immunological assay, for example, ELISA, immunostaining, or flow cytometry, using an antibody specific for the marker protein. The marker gene can be detected by use of a method of amplifying and/or detecting nucleic acid known in the art, for example, RT-PCR, microarray, or biochip. When the cells have an insert of a nucleotide sequence encoding a reporter protein (for example, Nano-Lantern (Saito K. et al., "Luminescent proteins for high-speed single-cell and whole-body imaging." Nat. Commun., 2012; 3: 1262)) downstream of the SOX10 gene, a marker gene of NCCs, and express a fusion protein of SOX10 and the reporter protein under the control of SOX10 promoter, a method for detecting the reporter protein (for example, measuring fluorescence intensity) may be used.

The effect equivalent to that exhibited by CHIR99021 with a "concentration of higher than 1 µM" (or a "concentration of higher than 1 µM and lower than 5 µM") as to the GSK3β inhibitor can be evaluated on the basis of GSK3β inhibitory activity. The GSK3β inhibitory activity of the GSK3β inhibitor can be measured by a method known per se and can be measured by, for example, a method described in Patsch et al., Nature cell biology, 2015, 17 (8): 994-1003 or Uno et al., Brain Res., 2009, 1296: 148-163. Specifically, the GSK3β inhibitory activity can be measured by using the gene expression regulation function (particularly, β-catenin phosphorylation function) of GSK3β in the Wnt/β-catenin pathway as an index. More specifically, such an approach involves: (i) culturing cells whose reporter gene expression is suppressed under the control of GSK3β, in the presence and absence of the GSK3β inhibitor; (ii) measuring an expression level of the reporter gene in the presence and absence of the GSK3β inhibitor; and (iii) determining the GSK3β inhibitory activity of the GSK3β inhibitor on the basis of an amount of increase in the expression level of the reporter gene in the presence of the GSK3β inhibitor with respect to the expression level of the reporter gene in the absence of the GSK3β inhibitor (see Example 9).

When the GSK3β inhibitor exhibits GSK3β inhibitory activity (% inhibition) equivalent to that exhibited by CHIR99021 with a concentration of higher than 1 μM in the measurement results, the GSK3β inhibitor is determined to exhibit the "effect equivalent to that exhibited by CHIR99021 (GSK3β inhibitory activity equivalent to the effect exhibited by CHIR99021) with a concentration of higher than 1 μM". In this context, the "equivalent" value (% inhibition) refers to a value which may vary up to plus or minus 30%, 25%, 20%, 15%, 10%, 8%, 6%, 5%, 4%, 3%, 2%, or 1% from the reference value. Preferably, the value refers to a range from minus or plus 15%, 10%, 5%, or 1% from the reference value.

The "effect equivalent to that exhibited by CHIR99021 with a "concentration of higher than 1 μM" (or a "concentration of higher than 1 μM and lower than 5 μM") as to the GSK3β inhibitor may be more suitably evaluated on the basis of a period for which the "neural crest cells that maintain multipotency" are culturable when the neural crest cells is cultured in the same way as a method described in Examples herein. When the "neural crest cells that maintain multipotency" are culturable, with the number thereof increased from that at the start of culture, by culture of the neural crest cells in a medium comprising the GSK3β inhibitor for a period equivalent to that of culture of the neural crest cells in a medium comprising CHIR99021 with a concentration of higher than 1 μM, the GSK3β inhibitor is determined to exhibit the "effect equivalent to that exhibited by CHIR99021 (neural crest cell proliferative activity equivalent to the effect exhibited by CHIR99021) with a concentration of higher than 1 μM". In this context, the "equivalent" value (period) refers to a value which may vary up to plus or minus 30%, 25%, 20%, 150, 100, 80, 60, 50, 40, 30, 20, or 1% from the reference value. Preferably, the value refers to a range of minus or plus 150, 100, 50, or 1% from the reference value.

In the case of using CHIR99021 itself as the GSK3β inhibitor, the concentration of the GSK3β inhibitor to be added is a concentration of higher than 1 μM, preferably 2 μM or higher and lower than 5 μM, more preferably higher than 2 μM and 4.5 μM or lower, particularly preferably 3 μM or higher and 4.5 μM or lower. The effect of allowing neural crest cells to proliferate while maintaining differentiation capacity for a long period has been found to be high for 2 μM or higher and lower than 5 μM CHIR99021 and to be highest, particularly, for 3 μM or higher and 4.5 μM or lower CHIR99021. Specifically, CHIR99021 with a concentration of 3 to 4.5 μM permitted culture and proliferation of neural crest cells that maintained multipotency over 112 days (16 weeks) or longer. Also, CHIR99021 with a concentration of 2 μM maintained multipotency over 9 weeks (63 days) or longer. On the other hand, 1 μM or 5 μM CHIR99021 decreased the number of cells that maintained multipotency on 3 weeks (21 days) and 6 weeks (42 days), respectively, of culture.

In the case of using CP21R7 as the GSK3β inhibitor, the concentration of the GSK3β inhibitor to be added is a concentration of higher than 0.1 μM, preferably 0.5 μM or higher, more preferably 1 μM or higher. The effect of allowing neural crest cells to proliferate while maintaining differentiation capacity for a long period has been found to be high for 0.5 μM or higher and 1 μM or lower CP21R7. Specifically, CP21R7 with a concentration of 0.5 to 1 μM permitted culture and proliferation of neural crest cells that maintained multipotency over 84 days (12 weeks) or longer. On the other hand, 0.1 μM CP21R7 decreased the number of cells that maintained multipotency on 3 weeks (21 days) of culture.

The concentration of bFGF to be added is not particularly limited and is, for example, 10 to 200 ng/ml, preferably 20 to 40 ng/ml.

The medium may be supplemented with a TGFβ inhibitor and/or an epidermal growth factor (EGF), in addition to the GSK3β inhibitor and bFGF. The TGFβ inhibitor mentioned above can be used without particular limitations.

The TGFβ inhibitor is preferably at least one member selected from the group consisting of SB431542, A83-01, LDN193189, Wnt3A/BIO, BMP4, GW788388, SM16, IN-1130, GW6604 and SB505124. The TGFβ inhibitor is particularly preferably SB431542.

The concentration of the TGFβ inhibitor to be added is appropriately adjusted depending on the type of the TGF3β inhibitor to be added and is, for example, 1 to 50 μM, preferably 5 to 20 μM.

In the case of using SB431542, the concentration of the TGFβ inhibitor to be added is not particularly limited and can be, for example, 1 to 40 μM, preferably 5 to 20 μM, particularly, 10 μM.

The concentration of EGF to be added is not particularly limited and is, for example, 5 to 100 ng/ml, preferably 20 to 40 ng/ml.

In the suspension culture, the neural crest cells obtained in the step (1) are detached from the culture container and then dispersed into a medium, and an aggregated cell mass is formed while medium components and the internal oxygen concentration of the medium are uniformized by stirring or shaking. The suitable stirring rate is appropriately set according to a cell density and the size of a culture container. Excessive stirring or shaking places physical stress on the cells and inhibits aggregated cell mass formation. Thus, the stirring or shaking rate is controlled so as to be able to uniformize medium components and the internal oxygen concentration of the medium and so as not to inhibit aggregated cell mass formation. The suspension culture may be performed by still standing without stirring or shaking.

The culture temperature is not particularly limited and is 30 to 40° C. (for example, 37° C.). A carbon dioxide concentration in the culture container is on the order of, for example, 5%.

The culture period in this step can be a period in which the cell number of interest is obtained. This step permits culture and proliferation of the neural crest cells that maintain multipotency over a long period. The ratio of the neural crest cells that maintain multipotency to the cultured cell population is at least 20% or more, 30% or more, or 40% or more and can be kept at preferably 50% or more, 60% or more, or 70% or more, more preferably 80% or more, 90% or more, or 95% or more.

During this culture, the cells are appropriately passaged. The passaging is performed every 5 to 8 days after inoculation, for example. Preferably, the interval between passages is a sufficient period for the expansion of the aggregated cell mass, and this period is shorter than that in which too large an aggregated cell mass hinders oxygen or nutrients from reaching the cells within the aggregated cell mass.

The period in which this step permits culture and proliferation of the neural crest cells that maintain multipotency is not particularly limited and may be, for example, 7 days, 14 days, 21 days, 28 days, 35 days, 42 days, 49 days, 56 days, 63 days, 70 days, 77 days, 84 days, 91 days, 98 days, 105 days, or 112 days or longer. This period is preferably 35 days or longer, more preferably 42 days or longer, further preferably 63 days or longer, particularly preferably 84 days or longer, most preferably 112 days or longer.

[Medium]

The present invention also provides a medium for use in the method for producing neural crest cells and the method for proliferating neural crest cells mentioned above, comprising neural crest cells. The preferred composition of the medium is as mentioned above.

[Cell Stock]

The present invention also provides a frozen stock comprising neural crest cells obtained by the method for producing neural crest cells and the method for proliferating neural crest cells mentioned above. The neural crest cells are positive to SOX10 expression and positive to expression of p75, a cell surface antigen marker of NCCs.

The frozen stock can be produced by separating the neural crest cells obtained by the method for producing neural crest cells and the method for proliferating neural crest cells from the medium, and suspending the neural crest cells in a cryopreservation solution for freezing. The separation of the neural crest cells from the medium can be performed using a cell strainer or centrifugation. The cells thus separated can be washed, if necessary. The frozen stock can comprise an additional cell population in addition to the neural crest cells and preferably comprises purified neural crest cells. The purification of the neural crest cells may be performed, for example, by separating the neural crest cells from other cell populations by cell sorting using the marker expression described above as an index. A conventional reagent for use in the cryopreservation of cells can be used as the cell preservation solution. For example, Cryostem Freezing Medium and CELLBANKER® are commercially available.

The frozen stock may be used as a starting material for inducing the differentiation of the neural crest cells to obtain nerve cells, glial cells, mesenchymal stromal cells, bone cells, chondrocytes, corneal cells and pigment cells. Also, the frozen stock may be used for preparing tissue models having the neural crest cells as a constituent.

[Method for Producing Various Cells from Neural Crest Cells]

The method for producing nerve cells, glial cells, mesenchymal stromal cells, bone cells, chondrocytes, corneal cells or pigment cells according to the present invention comprises the steps given below. Of these steps, the step (i) is the same as the step (2) of the method for producing neural crest cells according to the present invention or as the method for proliferating neural crest cells according to the present invention. (i) Suspension-culturing the neural crest cells in a medium comprising a GSK3β inhibitor and a basic fibroblast growth factor (bFGF), wherein the medium comprises the GSK3β inhibitor with a concentration that exhibits an effect equivalent to that exhibited by CHIR99021 with a concentration of higher than 1 μM; and (ii) allowing the neural crest cells obtained in the step (i) to differentiate into cells of at least one lineage selected from the group consisting of nerve cells, glial cells, mesenchymal stromal cells, bone cells, chondrocytes, corneal cells and pigment cells.

[Step of Induction into Various Cells]

According to the method for producing neural crest cells and the method for proliferating neural crest cells according to the present invention, neural crest cells that maintain multipotency to differentiate into nerve cells, glial cells and mesenchymal stromal cells or multipotency to differentiate into these cells as well as bone cells, chondrocytes, corneal cells and pigment cells can be obtained.

The induction of the differentiation of the neural crest cells into cells of each lineage selected from nerve cells, glial cells, mesenchymal stromal cells, bone cells, chondrocytes, corneal cells and pigment cells can be performed according to a known method described in a literature (for example, Non Patent Literatures 1 to 4).

Specifically, the induction of differentiation into nerve cells can be performed on the basis of a method described in Non Patent Literature 1 or 4.

For example, the neural crest cells are inoculated to a plate coated with fibronectin, and the medium is replaced with DMEM/F12 supplemented with N-2 Supplement (17502-048, Gibco), BDNF (028-16451, Wako Pure Chemical Industries, Ltd.), GDNF (074-06264, Wako Pure Chemical Industries, Ltd.), NT-3 (141-06643, Wako Pure Chemical Industries, Ltd.), and NGF (141-07601, Wako Pure Chemical Industries, Ltd.), followed by culture at 37° C. for 14 days under 5% $CO_2$.

Alternatively, the neural crest cells are inoculated to a plate and cultured for 1 day in CDM medium containing 10 μM SB431542 and 1 μM CHIR99021, and the medium is then replaced with Neurobasal medium (21103-049, Gibco) supplemented with B-27 Supplement (17504-044, Gibco), N-2 Supplement, L-glutamine (073-05391, Wako Pure Chemical Industries, Ltd.), Penicillin/Streptomycin (15140-122, Gibco), BDNF, GDNF, NT-3, and NGF, followed by culture at 37° C. for 35 days under 5% $CO_2$.

The cells thus cultured are fixed in 4% paraformaldehyde, and the emergence of differentiation into nerve cells expressing TUBB3 protein is confirmed by an immunostaining method.

The induction of differentiation into glial cells can be performed by an approach similar to the induction of differentiation into the nerve cells by the method described in Non Patent Literature 1 or 4. After the completion of the induction period of differentiation, the emergence of differentiation into glial cells is confirmed from the expression of GFAP protein.

The induction of differentiation into mesenchymal stromal cells can be performed on the basis of a method described in Non Patent Literature 1. Specifically, for example, the neural crest cells are inoculated at a density of $6.5 \times 10^4$ cells/$cm^2$ to a dish and cultured for 1 day in CDM medium containing 10 μM SB431542 and 1 μM CHIR99021. One day later, the medium is replaced with αMEM (Nacalai Tesque, Inc.) containing 10% fetal bovine serum (FBS, Nichirei Corp.). About 4 days later, morphological change in the cell is seen. The cells are passaged by detachment of the cells with 0.25% trypsin-EDTA (Gibco) and inoculation at a density of $1.0 \times 10^4$ cells/$cm^2$. 14 days after the start of induction of differentiation, the expression of CD73, CD44, CD45 and CD105, surface antigen markers of human mesenchymal stromal cells, is analyzed by FACS to confirm differentiation into mesenchymal stromal cells.

The induction of differentiation into bone cells can be performed on the basis of a method described in Non Patent Literature 1. Specifically, for example, the mesenchymal stromal cells described above are inoculated at $2.5 \times 10^5$ cells to a plate coated with fibronectin, and cultured for 2 weeks in αMEM containing 10% FBS, 0.1 μM dexa-methasone, 50 μg/ml ascorbic acid and 10 mM β-glycerophosphate. The medium is replaced once two days only for the first 1 week. A calcified nodule is detected by alizarin red staining to confirm differentiation into bone cells.

The induction of differentiation into chondrocytes can be performed on the basis of a method described in Non Patent Literature 1. Specifically, for example, the mesenchymal stromal cells described above are suspended at a concentration of 1.5×10³ cells/5 µl in DMEM:F12 (Invitrogen Corp.) containing 1% (v/v) ITS+ premix (BD), 0.17 mM AA2P, 0.35 mM proline (Sigma-Aldrich Co. LLC), 0.1 mM dexamethasone (Sigma-Aldrich Co. LLC), 0.15% (v/v) glucose (Sigma-Aldrich Co. LLC), 1 mM Na-pyruvate (Invitrogen Corp.), 2 mM GlutaMax, 0.05 mM MTG, 40 ng/ml PDGF-BB and 1% (v/v) FBS (Nichirei Corp.). 5 µl of the cell suspension is spotted onto a plate coated with fibronectin, and cultured for 1 hour. One hour later, 1 ml of the medium for induction of differentiation described above is added thereto. On 3 to 5 days after the start of induction of differentiation, 10 ng/ml TGFβ3 (R&D Systems, Inc.) is added thereto. On 10 days after the start of induction of differentiation, 50 ng/ml BMP4 is added thereto. The cells are cultured for 16 days, and the emergence of differentiation into chondrocytes is confirmed by alcian blue staining.

The induction of differentiation into corneal cells can be performed on the basis of a method described in Non Patent Literature 1. Specifically, for example, the neural crest cells are inoculated to a plate coated with fibronectin, and cultured for 1 day in CDM medium containing 10 µM SB431542 and 1 µM CHIR99021. One day later, the medium is replaced with a conditioned medium prepared by the culture of human corneal endothelial cells in CDM medium. The medium is replaced once two days. On 12 days after the start of induction of differentiation, the expression of ZO-1, a marker molecule of corneal cells, is confirmed by an immunostaining method, and the expression of COL4A1 and COL8A1 is confirmed by qPCR.

The induction of differentiation into pigment cells can be performed on the basis of a method described in Non Patent Literature 1. Specifically, for example, the neural crest cells are inoculated to a plate coated with fibronectin, and cultured for 1 day in CDM medium containing 10 µM SB and 1 µM CHIR. One day later, the medium is replaced with CDM medium containing 1 µM CHIR, 25 ng/ml BMP4 and 100 nM endothelin-3 (American Peptide Company). The medium is replaced once two days. On days 7 after the start of induction of differentiation, differentiation into pigment cell is confirmed from the expression of MITF and c-KIT genes.

The obtained nerve cells, glial cells, mesenchymal stromal cells, bone cells, chondrocytes, corneal cells and pigment cells may each be used as a cell preparation for regenerative medicine.

The neural crest cells are cells having multipotency to differentiate into many types of cells such as nerve cells, glial cells, mesenchymal stromal cells, bone cells, chondrocytes, corneal cells and pigment cells, and the ability to self-proliferate. The application of the neural crest cells to cell medicaments for regenerative medicine, etc. is expected on the basis of such ability found in the neural crest cells. If neural crest cells that maintain multipotency can be efficiently maintained or allowed to proliferate, their large-scale production is possible. If a stock of the neural crest cells that maintain multipotency can be prepared, the stock is useful as a raw material for cell medicaments. For example, use of cells (e.g., neural crest cells) positioned midway the differentiation of stem cells into the cells of interest (for example, nerve cells) as a starting material has been studied for the purpose of, for example, simplifying production methods, shortening production periods, or reducing production cost in the production of cell medicaments. The present invention is considered able to product a useful technique for this purpose. This may hold true not only for the production of cell medicaments but for the construction of screening systems using various cells, etc.

EXAMPLES

Example 1: Expansion Culture of Neural Crest Cells

[Induction of Differentiation of iPSCs into NCCs]

Human iPSCs were allowed to differentiate into neural crest cells (NCCs) according to the method described in Non Patent Literature 1. The iPSCs used were SOX10-Nano-Lantern Reporter Human iPSCs (201B7 line) described in Non Patent Literature 4. This cell line has an insert of a nucleotide sequence encoding a fluorescent protein Nano-Lantern (Saito K. et al., "Luminescent proteins for high-speed single-cell and whole-body imaging." Nat. Commun., 2012; 3: 1262) downstream of SOX10 gene, a marker gene of NCCs, and expresses a fusion protein of SOX10 and Nano-Lantern under the control of SOX10 promoter.

iPSCs were inoculated to a Matrigel-coated dish, adherent-cultured for 4 days in TeSR1 medium, and then adherent-cultured for 10 days in CDM medium containing 10 µM SB431542 (TGFβ inhibitor) and 1 µM CHIR99021 (GSK3β inhibitor), and thereby allowed to differentiate into NCCs.

[Expansion Culture of NCCs]

NCCs were detached from the dish and suspension-cultured in CDM medium containing 10 µM SB431542, 3 µM CHIR99021, 40 ng/ml bFGF and 40 ng/ml EGF. The cells were passaged every 7 days.

Figure 2:
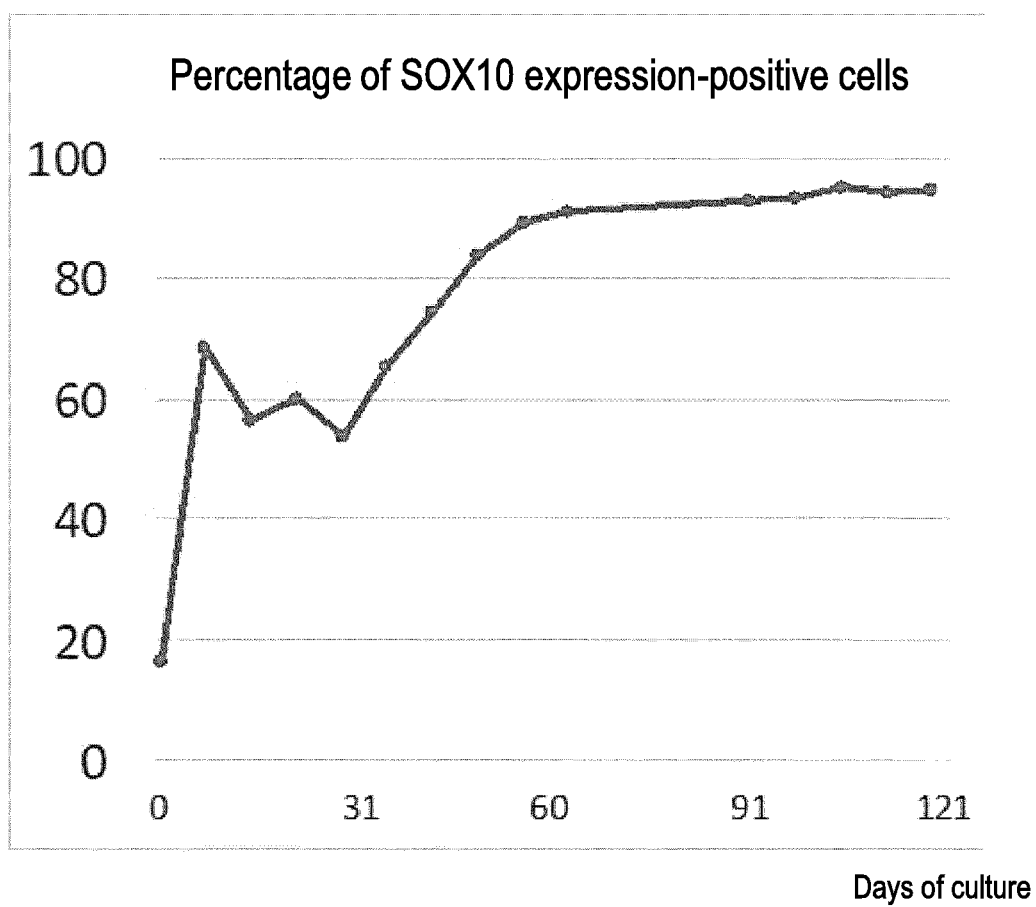
FIG. 2 is a graph showing change in the percentage of SOX10 expression-positive cells after the start of expansion culture of neural crest cells (Example 1). The ordinate shows the percentage of SOX10 expression-positive cells (%). The abscissa shows days of culture.

Change in total cell number after the start of expansion culture is shown in FIG. 1, and change in the percentage of SOX10 expression-positive cells is shown in FIG. 2. In order to measure the percentage of SOX10 expression-positive cells, an aggregated cell mass was dissociated using StemPro Accutase Cell Dissociation Reagent (Invitrogen Corp.) to prepare single-cell suspensions. The single-cell suspensions in FACS buffer (2% BSA HBSS) supplemented with 1 µg/mL PI (propidium iodide, Wako Pure Chemical Industries, Ltd.) were filtered through a tube with 35 µm nylon mesh (BD Falcon) and then analyzed using a flow cytometer (FACS Aria, BD Biosciences) to measure the ratio of GFP-positive cells in live cells (PI-negative cells). The total cell number was increased over the whole period, and a high percentage of SOX10 expression-positive cells was confirmed even on 121 days of culture. The expressed SOX10 serves as a marker of NCCs having multipotency. These results indicate that NCCs proliferate while maintaining differentiation capacity over a long culture period.

Example 2: Study on Concentration of Medium Additive

The GSK3β inhibitor, bFGF and EGF were studied for the influence of their concentrations on the ability of NCCs to self-proliferate and their differentiation capacity in the expansion culture of the NCCs. Hereinafter, the expansion culture was performed under the same conditions as in Example 1 unless otherwise specified.

Figure 3:
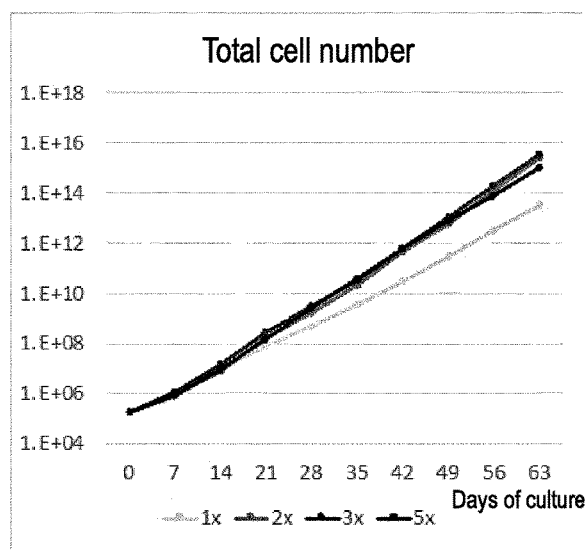
FIG. 3 is a graph showing results of measuring change in the total cell number of neural crest cells expansion-cultured by setting the concentrations of bFGF and EGF to 20 ng/ml (A) or 40 ng/ml (B) and setting the concentration of CHIR99021 to 1, 2, 3 or 5 μM (indicated by 1×, 2×, 3×, and 5×, respectively) (Example 2). The ordinate shows the total cell number, and "1.E+" represents a multiplier of 10. For example, "1.E+04" means 10000 cells. The abscissa shows days of culture.
Figure 3:
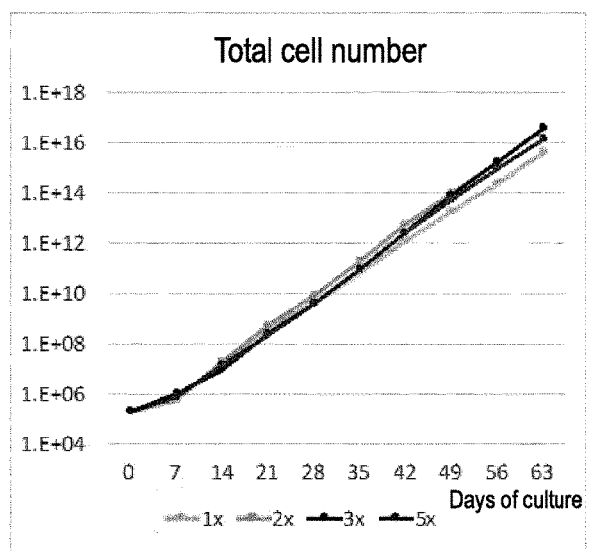
Figure 4:
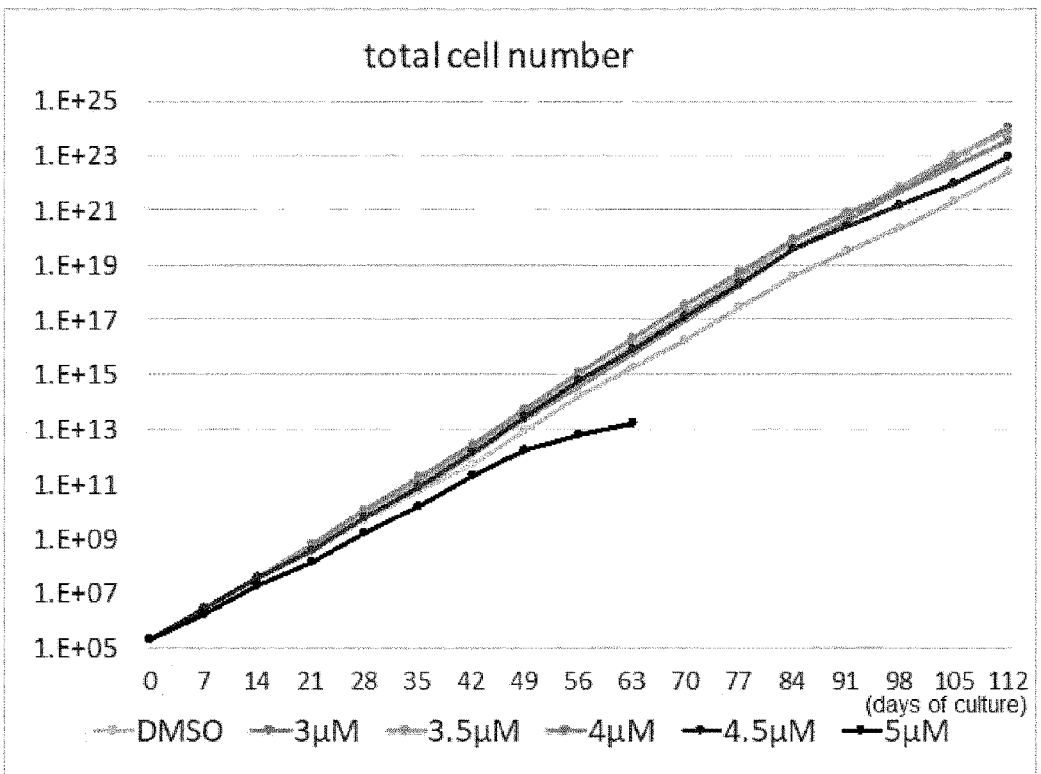
FIG. 4 is a graph showing results of measuring change in the total cell number of neural crest cells expansion-cultured by setting the concentrations of bFGF and EGF to 40 ng/ml and setting the concentration of CHIR99021 to 3, 3.5, 4, 4.5 or 5 μM (Example 2). The ordinate shows the total cell number, and "1.E+" represents a multiplier of 10.

FIG. 3 shows change in total cell number when the concentrations of bFGF and EGF were set to 20 ng/ml (A) or 40 ng/ml (B) and the concentration of CHIR99021 was set to 1, 2, 3, or 5 µM. The rate of cell proliferation for 1 week at the CHIR99021 concentration of 1 µM or 2 µM was 8- to 30-fold (also see Example 8 mentioned later). FIG. 4 shows change in total cell number when the concentrations of bFGF and EGF were set to 40 ng/ml and the concentration of CHIR99021 was set to 3, 3.5, 4, 4.5, or 5 µM. The concentrations of bFGF, EGF and CHIR99021 had no influence on change in total cell number.

Figure 5:
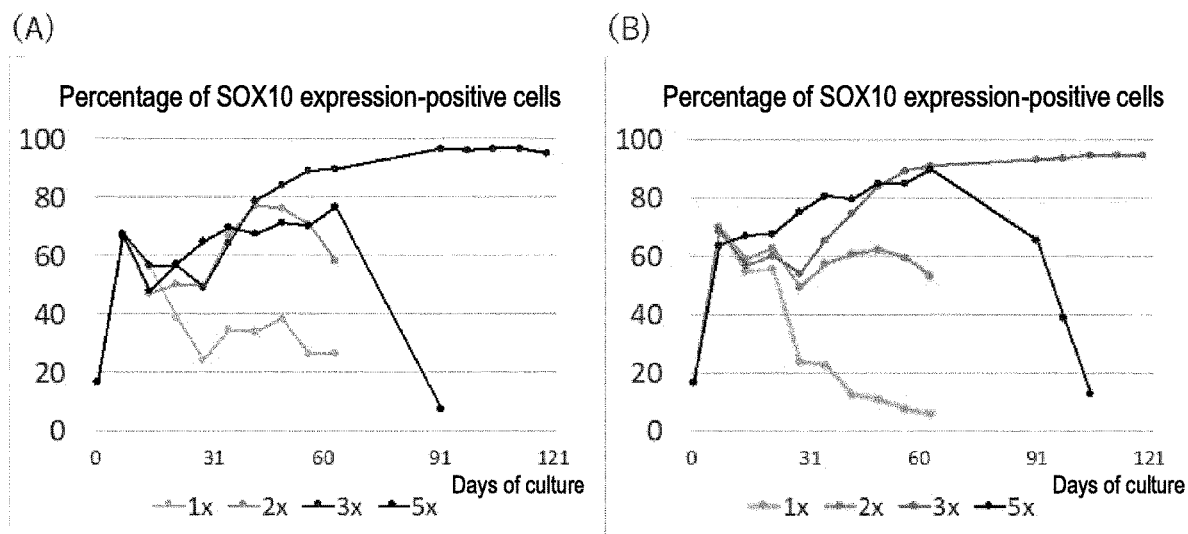
FIG. 5 is a graph showing results of measuring change in the percentage of SOX10 expression-positive cells of neural crest cells expansion-cultured by setting the concentrations of bFGF and EGF to 20 ng/ml (A) or 40 ng/ml (B) and setting the concentration of CHIR99021 to 1, 2, 3 or 5 μM (indicated by 1×, 2×, 3×, and 5×, respectively) (Example 2). The ordinate shows the percentage of SOX10 expression-positive cells (%). The abscissa shows days of culture.
Figure 6:
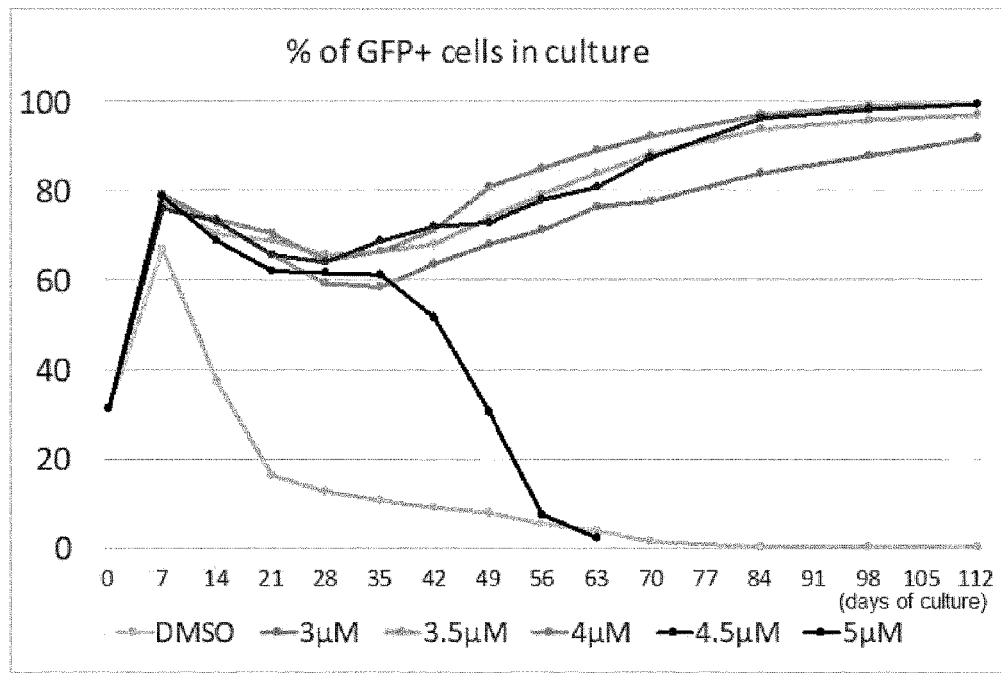
FIG. 6 is a graph showing results of measuring change in the percentage of SOX10 expression-positive cells of neural crest cells expansion-cultured by setting the concentrations of bFGF and EGF to 40 ng/ml and setting the concentration of CHIR99021 to 3, 3.5, 4, 4.5 or 5 μM (Example 2). The ordinate shows the percentage of SOX10 expression-positive cells (%). The abscissa shows days of culture.

FIG. 5 shows change in the percentage of SOX10 expression-positive cells when the concentrations of bFGF and EGF were set to 20 ng/ml (A) or 40 ng/ml (B) and the concentration of CHIR99021 was set to 1, 2, 3, or 5 µM. FIG. 6 shows change in the percentage of SOX10 expression-positive cells when the concentrations of bFGF and EGF were set to 40 ng/ml and the concentration of CHIR99021 was set to 3, 3.5, 4, 4.5, or 5 µM. When the concentration of CHIR99021 was 3 to 4.5 µM, 90% or more SOX10 expression-positive cells were confirmed in the long culture period (on 121 days of culture). Even when the concentration of CHIR99021 was 2 µM, about 55% or more SOX10 expression-positive cells were confirmed in the relatively long culture period (on 63 days of culture). On the other hand, when the concentration of CHIR99021 was 5 µM, about 55% or more percentage of SOX10 expression-positive cells were maintained up to 42 days of culture whereas the percentage of SOX10 expression-positive cells was decreased to about 5% or less on 63 days of culture. When the concentration of CHIR99021 was 1 µM, decrease in the percentage of SOX10 expression-positive cells was observed in the short culture period (on 21 days of culture), and the percentage of SOX10 expression-positive cells was about 25% or less on 63 days of culture. The concentrations of bFGF and EGF1 had no influence on change in the percentage of SOX10 expression-positive cells.

Example 3: Study on GSK3β Inhibitor

NCCs were expansion-cultured in the same way as in Example 1 except that the GSK3β inhibitor used in the expansion culture of the NCCs was changed from CHIR99021 to CP21R7. The concentration of CP21R7 was set to 0.1, 0.5 or 1 µM.

Figure 7:
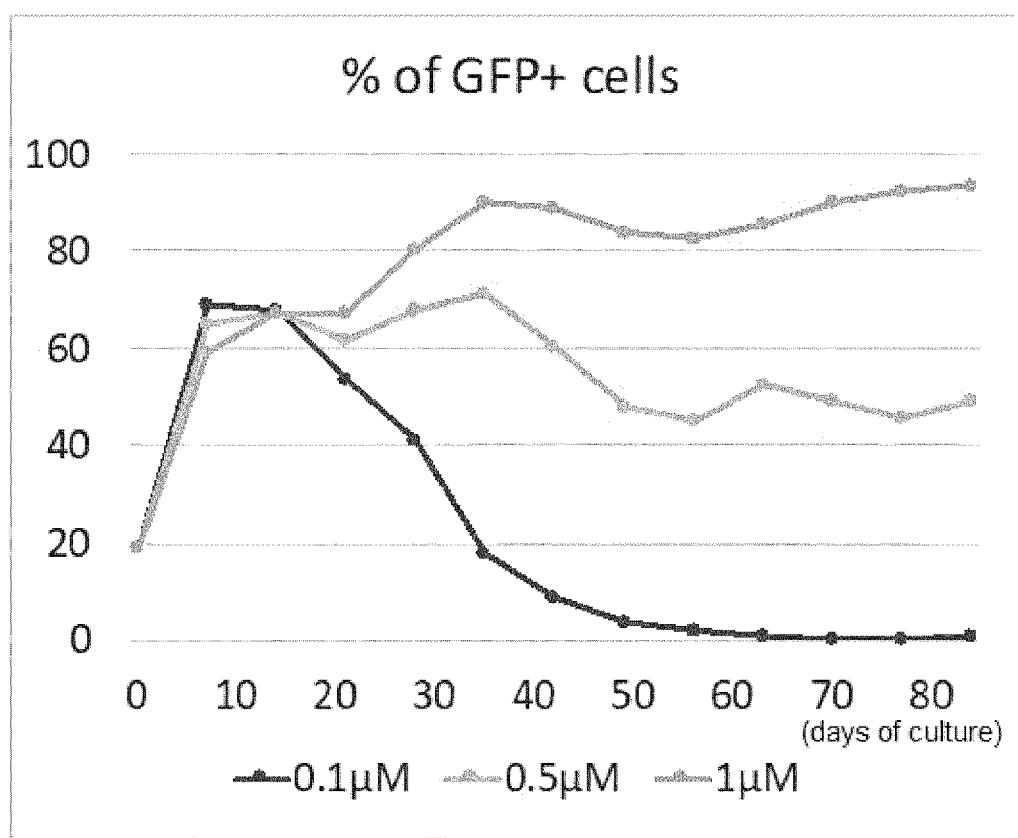
FIG. 7 is a graph showing change in the percentage of SOX10 expression-positive cells after the start of expansion culture of neural crest cells using CP21R7 as a GSK3β inhibitor (Example 3). The ordinate shows the percentage of SOX10 expression-positive cells (%). The abscissa shows days of culture.

Change in the percentage of SOX10 expression-positive cells is shown in FIG. 7. At the CP21R7 concentration of 0.5 or 1 µM, a high percentage of SOX10 expression-positive cells was confirmed even on 84 days of culture. On the other hand, at the CP21R7 concentration of 0.1 µM, the percentage of SOX10 expression-positive cells started to decrease in the short culture period (on 21 days of culture).

Example 4: Induction of Differentiation of Neural Crest Cells into Nerve Cells

The differentiation capacity of NCCs expansion-cultured in Example 1 into nerve cells was confirmed.

The induction of differentiation into nerve cells was performed on the basis of the method described in Non Patent Literature 4.

NCCs expansion-cultured by maintenance culture for 30 days were inoculated at 5×10$^5$ cells to a plate and cultured for 1 day in CDM medium containing 10 µM SB431542 and 1 µM CHIR99021. One day later, the medium was replaced with Neurobasal medium (21103-049, Gibco) supplemented with B-27 Supplement (17504-044, Gibco), N-2 Supplement (17502-048, Gibco), L-glutamine (073-05391, Wako Pure Chemical Industries, Ltd.), Penicillin/Streptomycin (15140-122, Gibco), BDNF (028-16451, Wako Pure Chemical Industries, Ltd.), GDNF (074-06264, Wako Pure Chemical Industries, Ltd.), NT-3 (141-06643, Wako Pure Chemical Industries, Ltd.), and NGF (141-07601, Wako Pure Chemical Industries, Ltd.), followed by culture at 37° C. for 35 days under 5% $CO_2$. During this culture period, the medium was replaced with every 3 to 4 days.

The cells were fixed by the addition of 4% paraformaldehyde (Wako Pure Chemical Industries, Ltd.) and incubation at 4° C. for 1 hour. The cells were reacted with an anti-TUBB3 antibody (845502, BioLegend, Inc.) and an anti-GFAP antibody (ab7260, Abcam PLC) as primary antibodies, further reacted sequentially with an Alexa 488-labeled secondary antibody (Invitrogen Corp.) and an Alexa 568-labeled secondary antibody as secondary antibodies compatible with the immunized animal species of the primary antibodies, and then observed under a fluorescence microscope.

The emergence of differentiation into nerve cells expressing the TUBB protein and glial cells expressing the GFAP protein was confirmed from the NCCs maintenance-cultured for 30 days.

The differentiation capacity into nerve cells was further confirmed in the same way as above using NCCs expansion-cultured by maintenance culture for 84 days. As a result, differentiation into nerve cells (peripherin-positive cells) and glial cells (GFAP-positive cells) was confirmed.

Example 5: Induction of Differentiation of Neural Crest Cells into Pigment Cells The differentiation capacity of NCCs expansion-cultured in Example 1 into nerve cells was confirmed.

The induction of differentiation into melanocytes was performed on the basis of the method described in Non Patent Literature 1.

NCCs expansion-cultured by maintenance culture for 84 days were inoculated to a 6-well plate coated with fibronectin, and cultured for 1 day in CDM medium containing 10 µM SB431542 and 1 µM CHIR99021. One day later, the medium was replaced with CDM medium supplemented with BMP4 and endothelin-3 (Wako Pure Chemical Industries, Ltd.), followed by culture at 37° C. for 7 days under 5% $CO_2$. During this culture period, the medium was replaced with every 2 days.

The cells were fixed by the addition of 4% paraformaldehyde (Wako Pure Chemical Industries, Ltd.) and incubation at 4° C. for 1 hour. The cells were reacted with an anti-MITF antibody (Sigma-Aldrich Co. LLC) as a primary antibody, further reacted sequentially with an Alexa 568-labeled secondary antibody (Invitrogen Corp.) as a secondary antibody compatible with the immunized animal species of the primary antibody, and then observed under a fluorescence microscope. The emergence of differentiation into melanocytes expressing the MITF protein was confirmed from the NCCs maintenance-cultured for 84 days.

Example 6: Induction of Differentiation of Neural Crest Cells into Mesenchymal Stromal Cells The differentiation capacity of NCCs expansion-cultured in Example 1 into mesenchymal stromal cells was confirmed.

The induction of differentiation into mesenchymal stromal cells was performed on the basis of the method described in Non Patent Literature 1.

NCCs expansion-cultured by maintenance culture for 84 days were inoculated to a dish for cell culture of 6 cm in diameter coated with fibronectin, and cultured for 1 day in CDM medium containing 10 µM SB431542 and 1 µM CHIR99021. One day later, the medium was replaced with CTS StemPro MSC SFM (Gibco, A1033201). The cells were passaged by dissociation of the cells with StemPro Accutase Cell Dissociation Reagent (Invitrogen Corp.) and inoculation at a density of 1.0 to 2.0×10⁶ cells/dish (for the 10-cm dish).

14 days after the start of induction of differentiation into mesenchymal stromal cells, the NCCs were immunostained with CD73 antibody (BD), CD44 antibody (BD), CD45 antibody (BD) and CD105 antibody (eBioscience, Inc.), antibodies against surface antigen markers of human mesenchymal stromal cells, followed by FACS analysis. The emergence of differentiation into mesenchymal stromal cells expressing each of the CD44, CD73 and CD0105 proteins and expressing no CD45 protein was confirmed from the NCCs maintenance-cultured for 84 days.

Example 7: Induction of Differentiation of Neural Crest Cells into Bone Cells, Chondrocytes or Adipocytes The differentiation capacity of NCCs expansion-cultured in Example 1 into bone cells, chondrocytes or adipocytes was confirmed.

The induction of differentiation into bone cells, chondrocytes or adipocytes was performed on the basis of the method described in Non Patent Literature 1.

NCCs expansion-cultured by maintenance culture for 84 days were allowed to differentiate into mesenchymal stromal cells by the method described in Example 6. The mesenchymal stromal cells were inoculated at 4.0×10⁴ cells/well to a 12-well plate coated with fibronectin, and cultured for 4 weeks in αMEM containing 10% FBS, 0.1 μM dexamethasone, 50 μg/ml ascorbic acid and 10 mM β-glycerophosphate to induce differentiation into bone cells. The medium was replaced once two to three days. A calcified nodule was detected by alizarin red staining to confirm differentiation into bone cells.

The induction of differentiation into chondrocytes was performed as follows: mesenchymal stromal cells into which the differentiation of NCCs expansion-cultured by maintenance culture for 84 days was induced was suspended at a concentration of 1.5×10³ cells/5 μl in DMEM:F12 (Invitrogen Corp.) containing 1% (v/v) ITS+ premix (BD), 0.17 mM AA2P, 0.35 mM proline (Sigma-Aldrich Co. LLC), 0.15% (v/v) glucose (Sigma-Aldrich Co. LLC), 1 mM Na-pyruvate (Invitrogen Corp.), 2 mM GlutaMax, 0.05 mM MTG, 40 ng/ml PDGF-BB and 1% (v/v) FBS (Nichirei Corp.). The cell suspension was spotted at 5 μl/well onto a 12-well plate coated with fibronectin, and cultured for 1 hour. One hour later, a medium further supplemented with 10 ng/ml TGFβ3 (R&D Systems, Inc.) and 100 ng/ml BMP7 (Wako Pure Chemical Industries, Ltd.) was added thereto at 1 ml/well. The cells were cultured for 10 days, and the emergence of differentiation into chondrocytes was confirmed by alcian blue staining.

The induction of differentiation into adipocytes was performed as follows: mesenchymal stromal cells into which the differentiation of NCCs expansion-cultured by maintenance culture for 84 days was induced was inoculated at 4.0×10⁴ cells/well to a 24-well plate coated with fibronectin, and cultured for 4 weeks in a medium attached to hMSC—Human Mesenchymal Stem Cell Adipogenic Differentiation Medium Bullet Kit (Lonza Japan Ltd.). The medium was replaced once two to three days. Oil droplets within cells stained by oil red 0 staining were detected to confirm differentiation into adipocytes.

The alizarin red S staining of the bone cells was performed as follows: the cells were fixed by the addition of 100% ethanol and incubation at room temperature for 10 minutes. The cells were reacted with Alizarin-Red staining Solution (Merck Millipore), washed with water, dried, and then observed under a microscope.

The alcian blue staining of the chondrocytes was performed as follows: the cells fixed by the addition of 4% paraformaldehyde (Wako Pure Chemical Industries, Ltd.) and incubation at room temperature for 30 minutes were reacted with 1% alcian blue staining solution (Muto Pure Chemicals Co., Ltd.), washed with water, and dried.

The oil red 0 staining of the adipocytes was performed as follows: the cells were fixed in 10% formalin at room temperature for 1 hour, reacted with a 3:2 mixture of a 0.5% dilution of Oil Red 0 Solution with isopropanol, and water at room temperature for 1 hour, and washed with water. The oil droplets were observed under a microscope.

Example 8: Study on Concentration of Medium Additive—2 bFGF was studied for the influence of its concentration on the ability of NCCs to self-proliferate and their differentiation capacity in the expansion culture of the NCCs. Hereinafter, the expansion culture was performed under the same conditions as in Example 1 unless otherwise specified.

Figure 8:
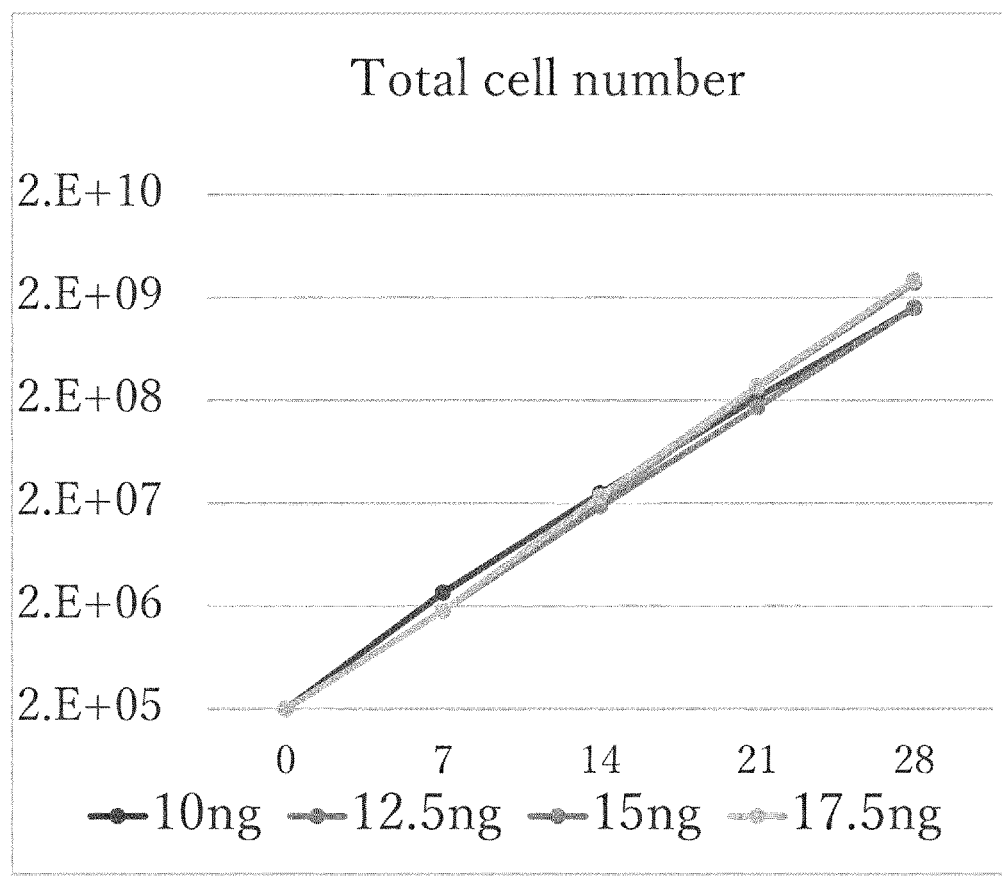
FIG. 8 is a graph showing results of measuring change in the total cell number of neural crest cells expansion-cultured by setting the concentration of bFGF to 10, 12.5, 15.0, or 17.5 ng/ml (Example 8). The ordinate shows the total cell number, and "1.E+" represents a multiplier of 10.
Figure 9:
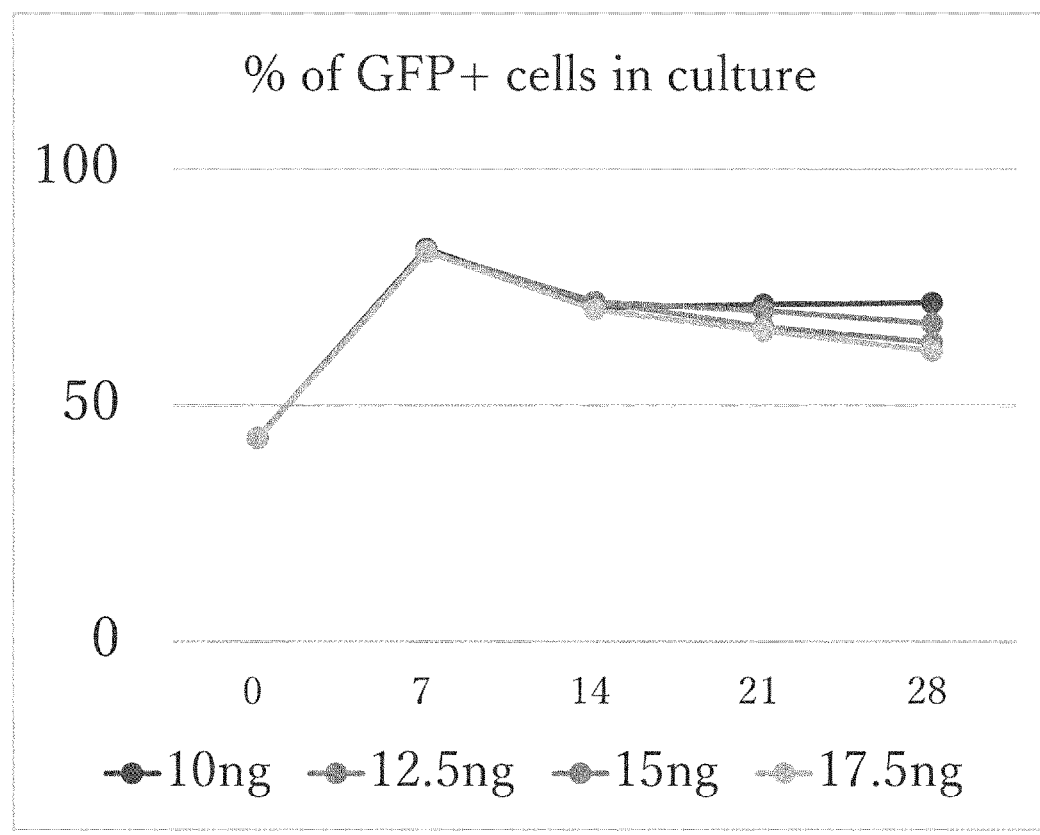
FIG. 9 is a graph showing results of measuring change in the percentage of SOX10 expression-positive cells total cell number of neural crest cells expansion-cultured by setting the concentration of bFGF to 10, 12.5, 15.0, or 17.5 ng/ml (Example 8). The ordinate shows the percentage of SOX10 expression-positive cells (%). The abscissa shows days of culture.

FIG. 8 shows change in total cell number when the concentration of CHIR99021 was set to 1.5 μM and the concentration of bFGF was set to 10, 12.5, 15.0, or 17.5 ng/ml. FIG. 9 shows change in the percentage of SOX10 expression-positive cells. The bFGF concentration had no influence on the percentage of SOX10 expression positivity.

The behavior of change in total cell number was substantially the same within the bFGF concentration range described above, and the rate of cell proliferation was within the range of 6- to 13-fold for 1 week. The rate of cell proliferation for 1 week in Example 2 was within a higher range of 8- to 30-fold at the CHIR99021 concentration of 1 μM or 2 μM and the bFGF concentration of 20 ng/ml or 40 ng/ml (see FIG. 3), suggesting that bFGF contributes to the ability of NCCs to self-proliferate and has a suitable concentration range of 20 to 40 ng/ml.

Example 9: Measurement of GSK3β Inhibitory Activity

An experimental system for evaluating the GSK3β inhibitory activity of the GSK3β inhibitor was established.

In the Wnt/β-catenin pathway, GSK3β functions to phosphorylate β-catenin in the absence of Wnt-ligand. The phosphorylated β-catenin is ubiquitinated and degraded within the proteasome. Therefore, gene expression downstream of the Wnt-β-catenin pathway is suppressed. If GSK3β in this pathway is inhibited, β-catenin is translocated into the nucleus, without being degraded, to induce gene expression downstream of the Wnt-β-catenin pathway together with other transcription factors such as T-cell factor (TCF)/lymphoid enhancer factor (LEF). CellSensor LEF/TCF-bla HCT-116 Cell Line (Thermo Fisher Scientific Inc., K1676) stably incorporates therein LEF/TCF and incorporates a reporter gene (beta-lactamase reporter gene) so as to express the reporter gene under the control of LEF/TCF. The expression of the reporter gene in this cell line in the absence of the Wnt-ligand serves as an index for the inhibition of the function (β-catenin phosphorylation function) of GSK3β.

The GSK3β inhibitory activity of the GSK3β inhibitor was measured by assay using this cell line.

The assay was conducted in accordance with the protocol of Invitrogen Corp. (CellSensor® LEF/TCF-bla HCT 116 Cell-based Assay Protocol).

Specifically, LEF/TCF-bla HCT-116 Cells were suspended in an assay medium (OPTI-MEM, 0.5% dialyzed FBS, 0.1 mM NEAA, 1 mM sodium pyruvate, 100 U/mL/ 100 μg/mL Pen/Strep) (312,500 cells/mL). The cell suspension was inoculated to each well of an assay plate (10,000 cells/well), and cultured for 16 to 24 hours.

The GSK3β inhibitor (CHIR99021 was used here) was added to each well (concentration: 0.316, 1.00, 3.16, 10.0, 31.6, 100, 316, 1000, 3160, and 10000 nM), and the cells were cultured for 5 hours.

A beta-lactamase substrate solution (LiveBLAzer-FRET B/G (CCF4-AM) Substrate Mixture) was added to each well (8 μL/well) and incubated for 2 hours. A fluorescence value was measured in a fluorescence plate reader. The measurement was performed in two wells per each concentration condition.

The results are shown in "Table 1". The GSK3β inhibitory activity exhibited by 1 μM CHIR99021 was 113.5 (mean from the two wells) in terms of the fluorescence value.

The concentration that exhibits GSK3β inhibitory activity equivalent to that exhibited by 1 μM CHIR99021 (fluorescence value: 113.5) can also be determined as to GSK3β inhibitors other than CHIR99021 by measuring fluorescence values under each concentration condition using this experimental system and preparing calibration curves according to the standard method.

TABLE 1

| Compound concentration | Fluorescence value | |
| --- | --- | --- |
| (nM) | Well 1 | Well 2 |
| 10000 | 88 | 73 |
| 3160 | 99 | 136 |
| 1000 | 114 | 113 |
| 316 | 101 | 96 |
| 100 | 75 | 60 |
| 31.6 | 21 | 45 |
| 10.0 | 12 | 23 |
| 3.16 | 0 | 14 |
| 1.00 | 0 | 0 |
| 0.316 | 6 | 0 |

The invention claimed is:

1. A method for producing neural crest cells and maintaining their multipotency, comprising the steps of:
(1) obtaining neural crest cells by inducing the differentiation of stem cells into the neural crest cells; and
(2) suspension-culturing the neural crest cells in a medium comprising a GSK3β inhibitor and a basic fibroblast growth factor, wherein the medium comprises the GSK3β inhibitor with a concentration that exhibits an effect equivalent to that exhibited by CHIR99021 with a concentration of 3.0 μM to 4.5 μM, thereby maintaining multipotent neural crest cells over 63 days or longer, wherein the cultured neural crest cells comprise a ratio of at least 75% or more of neural crest cells that maintain multipotency to cultured cell population.

2. The production method according to claim 1, wherein the medium further comprises a TGFβ inhibitor.

3. The production method according to claim 2, wherein the TGFβ inhibitor is at least one member selected from the group consisting of SB431542, A83-01, LDN193189, Wnt3a/BIO, BMP4, GW788388, SM16, IN-1130, GW6604 and SB505124.

4. The production method according to claim 1, wherein the medium is chemically defined medium (CDM) medium.

5. The production method according to claim 1, wherein the medium further comprises an epidermal growth factor.

6. The production method according to claim 1, wherein the GSK3β inhibitor is at least one member selected from the group consisting of CHIR99021, CP21R7, CHIR98014, LY2090314, kenpaullone, AR-A0144-18, TDZD-8, SB216763, BIO, TWS-119 and SB415286.

7. The production method according to claim 6, wherein the GSK3β inhibitor is CHIR99021.

8. The production method according to claim 1, wherein in the step (2), the neural crest cells are passaged every 5 to 8 days after inoculation.

9. The production method according to claim 1, wherein the cultured neural crest cells that maintain multipotency over 77 days or longer, and wherein the cultured neural crest cells comprise a ratio of at least 80% or more of neural crest cells that maintain multipotency to cultured cell population.

10. The production method according to claim 1, wherein the cultured neural crest cells that maintain multipotency over 121 days or longer, and wherein the cultured neural crest cells comprise a ratio of at least 90% or more of neural crest cells that maintain multipotency to cultured cell population.

11. A method for proliferating neural crest cells and maintaining their multipotency, comprising the step of:
(I) suspension-culturing the neural crest cells in a medium comprising a GSK3β inhibitor and a basic fibroblast growth factor, wherein the medium comprises the GSK3β inhibitor with a concentration that exhibits an effect equivalent to that exhibited by CHIR99021 with a concentration of 3.0 μM to 4.5 μM higher than 1 μM and lower that 5 μM, thereby maintaining multipotent neural crest cells over 63 days or longer, wherein the cultured neural crest cells comprise a ratio of at least 75% or more of neural crest cells that maintain multipotency to cultured cell population.

12. The method according to claim 11, wherein the cultured neural crest cells that maintain multipotency over 77 days or longer, and wherein the cultured neural crest cells comprise a ratio of at least 80% or more of neural crest cells that maintain multipotency to cultured cell population.

13. The method according to claim 11, wherein the cultured neural crest cells that maintain multipotency over 121 days or longer, and wherein the cultured neural crest cells comprise a ratio of at least 90% or more of neural crest cells that maintain multipotency to cultured cell population.

14. A method for producing nerve cells, glial cells, mesenchymal stromal cells, bone cells, chondrocytes, corneal cells or pigment cells, comprising the steps of:
(i) suspension-culturing neural crest cells in a medium comprising a GSK3β inhibitor and a basic fibroblast growth factor, wherein the medium comprises the GSK3β inhibitor with a concentration that exhibits an effect equivalent to that exhibited by CHIR99021 with a concentration 3.0 μM to 4.5 μM higher than 1 μM and lower that 5 μM, thereby maintaining multipotent neural crest cells over 63 days or longer, wherein the cultured neural crest cells comprise a ratio of at least 75% or more of neural crest cells that maintain multipotency to cultured cell population; and (ii) differentiating the neural crest cells obtained in the step (i) into cells of at least one lineage selected from the group consisting of nerve cells, glial cells, mesenchymal stromal cells, bone cells, chondrocytes, corneal cells and pigment cells.

15. A method for culturing neural crest cells and extending their multipotency 63 days or longer, comprising the steps of:
    (1) obtaining neural crest cell by inducing the differentiation of stem cells into the neural crest cells; and
    (2) suspension-culturing the neural crest cells in a medium comprising a GSK3β inhibitor and a basic fibroblast growth factor, wherein the medium comprises the GSK3β inhibitor with a concentration that exhibits an effect equivalent to that exhibited by CHIR99021 with a concentration 3.0 µM to 4.5 µM higher than 1 µM and lower that 5 µM, thereby maintaining multipotent neural crest cells over 63 days or longer, wherein the cultured neural crest cells comprise a ratio of at least 75% or more of neural crest cells that maintain multipotency to cultured cell population.

16. The method according to claim 15, wherein the cultured neural crest cells that maintain multipotency over 77 days or longer, and wherein the cultured neural crest cells comprise a ratio of at least 80% or more of neural crest cells that maintain multipotency to cultured cell population.

17. The method according to claim 15, wherein the cultured neural crest cells that maintain multipotency over 121 days or longer, and wherein the cultured neural crest cells comprise a ratio of at least 90% or more of neural crest cells that maintain multipotency to cultured cell population.

* * * * *